(12) United States Patent
Bonyuet et al.

(10) Patent No.: US 9,250,132 B2
(45) Date of Patent: Feb. 2, 2016

(54) METHODS AND SYSTEMS FOR CHEMICAL COMPOSITION MEASUREMENT AND MONITORING USING A ROTATING FILTER SPECTROMETER

(71) Applicant: Pason Systems Corp., Calgary (CA)

(72) Inventors: David Bonyuet, Watertown, MA (US); Vidi A. Saptari, Cambridge, MA (US)

(73) Assignee: Pason Systems Corp., Calgary, Alberta (CA)

(*) Notice: Subject to any disclaimer, the term of this patent is extended or adjusted under 35 U.S.C. 154(b) by 0 days.

(21) Appl. No.: 13/932,481

(22) Filed: Jul. 1, 2013

(65) Prior Publication Data

US 2013/0293893 A1   Nov. 7, 2013

Related U.S. Application Data

(63) Continuation of application No. 13/451,621, filed on Apr. 20, 2012, now Pat. No. 8,502,981, which is a continuation of application No. 12/427,485, filed on Apr. 21, 2009, now Pat. No. 8,184,293.

(60) Provisional application No. 61/084,985, filed on Jul. 30, 2008.

(51) Int. Cl.
*G01N 21/25* (2006.01)
*G01J 3/42* (2006.01)
(Continued)

(52) U.S. Cl.
CPC .... *G01J 3/42* (2013.01); *G01J 3/02* (2013.01); *G01J 3/0235* (2013.01); *G01J 3/06* (2013.01);
(Continued)

(58) Field of Classification Search
USPC .................................. 356/417, 418
See application file for complete search history.

(56) References Cited

U.S. PATENT DOCUMENTS 2,834,246 A   5/1958   Foskett
3,864,037 A   2/1975   Johnson
(Continued)

FOREIGN PATENT DOCUMENTS

WO   WO-2010/014277 A1   2/2010

OTHER PUBLICATIONS

International Search Report and Written Opinion, Application No. PCT/US2009/041254, dated Oct. 9, 2009, 16 pages.
(Continued)

*Primary Examiner* — Abdullahi Nur
(74) *Attorney, Agent, or Firm* — Choate, Hall & Stewart LLP; William R. Haulbrook

(57) ABSTRACT

The invention relates to methods and systems for measuring and/or monitoring the chemical composition of a sample (e.g., a process stream), and/or detecting specific substances or compounds in a sample, using light spectroscopy such as absorption, emission and fluorescence spectroscopy. In certain embodiments, the invention relates to spectrometers with rotating narrow-band interference optical filter(s) to measure light intensity as a function of wavelength. More specifically, in certain embodiments, the invention relates to a spectrometer system with a rotatable filter assembly with a position detector rigidly attached thereto, and, in certain embodiments, the further use of various oversampling methods and techniques described herein, made particularly useful in conjunction with the rotatable filter assembly. In preferred embodiments, the rotatable filter is tilted with respect to the rotation axis, thereby providing surprisingly improved measurement stability and significantly improved control of the wavelength coverage of the filter spectrometer.

28 Claims, 19 Drawing Sheets

(51) Int. Cl.
  G01J 3/02    (2006.01)
  G01J 3/06    (2006.01)
  G01J 3/32    (2006.01)
  G01N 21/27   (2006.01)
  G01N 21/31   (2006.01)
  G01J 3/12    (2006.01)
  G01N 21/33   (2006.01)
  G01N 21/3504 (2014.01)

(52) U.S. Cl.
  CPC ............... *G01J 3/32* (2013.01); *G01N 21/274* (2013.01); *G01N 21/314* (2013.01); *G01J 2003/1247* (2013.01); *G01N 21/33* (2013.01); *G01N 21/3504* (2013.01); *G01N 2021/3174* (2013.01); *G01N 2201/129* (2013.01)

(56) References Cited

U.S. PATENT DOCUMENTS

| | | | |
|---|---|---|---|
| 3,904,880 A | | 9/1975 | Benz et al. |
| 4,040,747 A | | 8/1977 | Webster |
| 4,563,090 A | | 1/1986 | Witte |
| 4,759,625 A | * | 7/1988 | Caponi et al. ............... 356/73.1 |
| 4,770,478 A | * | 9/1988 | Cross et al. ................. 359/359 |
| 4,988,196 A | * | 1/1991 | Gilligan ...................... 356/308 |
| 5,166,755 A | | 11/1992 | Gat |
| 5,218,473 A | | 6/1993 | Seddon et al. |
| 5,268,745 A | | 12/1993 | Goody |
| 5,581,356 A | | 12/1996 | Vezard |
| 5,663,894 A | | 9/1997 | Seth et al. |
| 6,057,925 A | | 5/2000 | Anthon |
| 6,229,402 B1 | | 5/2001 | Katoaka et al. |
| 6,496,309 B1 | | 12/2002 | Bliton et al. |
| 7,099,003 B2 | | 8/2006 | Saptari et al. |
| 7,436,515 B2 | | 10/2008 | Kaye et al. |
| 8,184,293 B2 | | 5/2012 | Bonyuet et al. |
| 8,502,981 B2 | | 8/2013 | Bonyuet et al. |
| 2003/0072680 A1 | * | 4/2003 | Higuchi et al. ............... 422/64 |
| 2006/0018514 A1 | * | 1/2006 | Bankhead ..................... 382/108 |
| 2006/0250606 A1 | | 11/2006 | Kaye et al. |
| 2008/0273208 A1 | | 11/2008 | Johansen et al. |
| 2015/0103354 A1 | | 4/2015 | Saptari |

OTHER PUBLICATIONS

International Preliminary Report on Patentability, Application No. PCT/US2009/041254, mailing date Feb. 10, 2011, 9 pages.
Saptari et al., Design of a mechanical tunable-filter spectrometer for noninvasive glucose measurement, Applied Optics 43(13):1 (2004).

* cited by examiner

METHODS AND SYSTEMS FOR CHEMICAL COMPOSITION MEASUREMENT AND MONITORING USING A ROTATING FILTER SPECTROMETER

RELATED APPLICATION

This Application is a continuation of U.S. patent application Ser. No. 13/451,621 filed on Apr. 20, 2012, which is a continuation application of U.S. patent application Ser. No. 12/427,485 filed on Apr. 21, 2009, which granted on May 22, 2012 as U.S. Pat. No. 8,184,293, which claims benefit of U.S. Provisional Patent Application No. 61/084,985 filed on Jul. 30, 2008, the disclosures of which are hereby incorporated herein by reference in their entireties.

FIELD OF THE INVENTION

The invention relates generally to spectroscopic methods and systems. More particularly, in certain embodiments, the invention relates to methods and systems for measuring and/or monitoring the chemical composition of a sample (e.g., a process stream), and/or detecting substances or compounds in a sample, using light spectroscopy.

BACKGROUND OF THE INVENTION

Several chemical composition measurement devices using light spectrometers are currently commercially available. Examples of the types of spectrometers currently used include Fourier transform infrared spectrometer (FTIR), dispersive spectrometer (spectrograph or monochromator) and linear variable filter (LVF) spectrometer. FTIR based devices use Michelson interferometers and have generally been considered to provide the highest performance, due to their high optical throughput, which enables high-sensitivity measurements. In contrast, dispersive and linear variable filter spectrometers have significantly lower optical throughput and thus lower sensitivity performance. However, dispersive and linear variable filter spectrometers generally provide simpler and more rugged instrumentation, and are less expensive to manufacture.

Another type of chemical composition measurement and monitoring device that is widely used, in particular, in the field of gas monitoring, is non-dispersive infrared (NDIR) devices. These devices use fixed narrowband optical filters to select a particular wavelength band region. They have high optical throughput, rivaling that of FTIR based devices, and thus provide high-sensitivity measurement. This type of device, however, is generally not considered to be a spectrometer, as it does not measure light intensity as a function of wavelength; rather, it provides a single measurement value corresponding to the light intensity at a particular wavelength band. For this reason, each device (employing one filter, one photo-detector and one light source) can only measure one compound. Therefore, such devices are not considered to be chemical "composition" measuring devices.

The transmitted wavelength band of a narrowband optical filter, such as that used in NDIR instruments, can be varied or "tuned" by varying the angle of incidence (U.S. Pat. No. 4,040,747 to Webster, 1977 and U.S. Pat. No. 2,834,246 to Foskett, 1958, both of which are incorporated herein by reference). Such methods enable the measurement of optical signals from multiple wavelengths or wavelength bands using only a single optical filter, light source and detector, thus potentially creating a simple, low-cost, high-throughput spectrometer.

One method of varying the incident angle is to continuously rotate the filter in one direction and capture the data at the relevant angular positions. This type of continuously-rotating filter spectrometers has been described (U.S. Pat. No. 4,040,747 to Webster, 1977, U.S. Pat. No. 2,834,246 to Foskett, 1958, U.S. Pat. No. 5,268,745 to Goody, 1993, U.S. Pat. No. 7,099,003 to Saptari, 2006, all of which are incorporated herein by reference). However, these devices have not been in significant commercial use. FTIR spectrometers, grating based spectrometers and LVF spectrometers are still by far the most commonly used hardware for chemical composition monitoring, despite the potential advantages for the rotating tunable filter instruments.

There are weaknesses of the previous rotating tunable filter systems which prevent them from being used in a commercial setting as chemical composition measuring or monitoring devices. For example, these systems lack measurement stability and robustness due to wavelength instability, spectral interferences, environmental variations and/or instrumental changes. Such systems also lack versatility, in particular, in that they are not able to provide wide spectral coverage. Furthermore, there are difficulties in volume manufacturing, in particular, difficulties in producing reproducible instruments that are interchangeable without each instrument requiring empirical sample based calibration.

SUMMARY OF THE INVENTION

The invention provides methods and systems for measuring and/or monitoring the chemical composition of a sample (e.g., a process stream in an industrial setting), using a spectrometer with rotating narrow-band interference optical filter(s). In preferred embodiments, the spectrometer system features a rotatable filter assembly with a position detector rigidly attached thereto, providing more accurate and robust detection. The rotatable filter is preferably tilted with respect to the rotation axis, thereby providing surprisingly improved measurement stability and significantly improved control of the wavelength coverage of the filter spectrometer. Also, in certain embodiments, the invention includes methods of using such spectrometers for measuring and monitoring chemical composition of compounds in gas, liquid and/or solid forms, for example, in both laboratory and non-lab (e.g., industrial) settings.

Various oversampling methods and techniques are also presented herein, which are found to be particularly useful when employed in conjunction with a spectrometer with the rotatable filter assembly feature as described herein. In certain embodiments, the invention includes methods of using such spectrometers for measuring and monitoring chemical composition of compounds in gas, liquid and/or solid forms, for example, in both laboratory and non-lab (e.g., industrial) settings.

In certain embodiments, the invention provides a rotating filter spectrometer for chemical composition measurement and monitoring, employs one or multiple light sources, one or multiple photo-detectors, one or multiple narrow-band optical interference filters, a DC motor, a position encoder, an analog-to-digital conversion device, and a computing unit. In preferred embodiments, the narrow-band optical filter(s) are rigidly mounted on a rotating mechanical assembly driven by a DC motor. The rotating filter assembly is positioned relative to a collimated light beam from the light source such that the axis of rotation is perpendicular to the light beam or, preferably, positioned such that the axis of rotation is slightly non-perpendicular to the light beam, such non-perpendicular conformation resulting in surprisingly improved measurement stability due to apparent suppression of back-reflected or stray light, and resulting in significantly improved control of the wavelength coverage of the filter spectrometer, given the filter characteristics and the angular coverage of the mechanical system.

In preferred embodiments, the rotating filter assembly rotates continuously in one angular direction. A rotary positional encoder is rigidly attached to the rotating filter assembly such that there is no relative displacement or mechanical "compliance" or "play" between it and the rotating filter assembly. The digital pulses generated by the encoder during motion are used to clock the analog-to-digital conversion of the signal collected by the photo-detector. Furthermore, the encoder and its processing electronics are designed, configured and/or selected in such a way that it produces significantly more pulses-per-rotation than what is required to accurately measure the relevant spectral features. The spectral signal is over-sampled. A convolution algorithm is then preferably applied to digitally process the recorded spectrum to enhance wavelength stability or repeatability and to improve spectral signal-to-noise ratio.

In certain embodiments, inherent or deliberately-introduced spectral features are used to lock the relative position of the encoder with respect to the rotating filter assembly. The spectral features may be those due to the spectral characteristics of the light source, system's optical components, and/or the sample compound itself. Such methods ensure wavelength stability despite alignment changes due to mechanical forces or temperature changes.

A variable gain amplifier is preferably employed to automatically adjust the photo-detector signal amplification gain in real-time. The gain profile may be scheduled based upon the location of the rotating filter assembly, or updated automatically based upon the magnitude of the received signal. Such a feature enables measurement of distinctly different spectral regions, such as measurement at the near infrared and the mid infrared regions simultaneously, without saturating the analog-to-digital circuitry. Similarly, the light source intensity may be varied to further optimize the measurement dynamic range and to better observe weak spectral features.

In certain embodiments, multiple regression regions and calibration matrices, combined with cross-analysis, are used to enhance robustness and accuracy of multi-compound measurement as well as measurement in highly complex sample matrices. Each calibration matrix can be optimized for a particular target compound or features of the target compounds. The effects of nonlinearities can be significantly suppressed.

In certain embodiments, an adaptive regression analysis is employed to account for spectral baseline variations that may have complex shapes due to the filter's non-linear wavelength-angle function. The algorithm automatically and continually updates to compensate for the baseline variations, as well as other spectral variations such as those due to light interactions with unknown, interfering compounds.

A differential measurement may be employed in applications monitoring certain processes or reactions, for example, where the input and output streams are available for analysis. The method suppresses the effects of instrumental and environmental changes, as well as minimizes the effects of sample background interferences.

Embodiments of the invention provide methods, systems (including apparatus) for chemical composition measurement and monitoring in gas, liquid and/or solid samples which utilize a single or multiple continuously rotating narrow-band filters. In certain embodiments, the invention provides negligible wavelength instability or drift due to various environmental disturbances such as vibrations and temperature variations over a long period of time. Embodiments of the invention also provide wide spectral or wavelength coverage with optimum use of the measurement dynamic range throughout the analysis range, suitable for simultaneous measurement and/or monitoring of multiple compounds. The systems effectively compensate for spectral baseline instability and can be built and manufactured consistently (without requiring extensive, individual-machine calibration) and relatively inexpensively.

The systems and methods can be used for continuous monitoring of gas, liquid, and/or solid chemical composition (% levels), for example, for monitoring production throughput and quality, e.g., in process streams. They can also be used for gas, liquid, or solid phase trace species monitoring (ppm or ppb levels), for example, impurity detection and monitoring, e.g., in process streams. Embodiments may also provide ambient monitoring for safety purposes. The systems and methods described herein may be applied, for example, in the petrochemical, bioreactor (biofuel), pharmaceutical, food and beverage, specialty chemical, and/or alternative energy industries.

For example, an embodiment of the invention provides combustion process monitoring (e.g., alternative energy production using a bioreactor) for the monitoring of any one or more of the following process gases: CO, $CO_2$, $O_2$, $CH_4$ (methane), $N_2O$ (nitrous oxide). In other embodiments, the invention provides systems and/or methods for monitoring trace levels (e.g., ppm or sub-ppm) of sulfur compounds (e.g., dimethyl sulfide, dimethyl disulfide, carbonyl sulfide, hydrogen sulfide, etc.) in a natural gas line, for example, in a fuel cell-based power plant. In yet another embodiment, the invention provides a system and/or method for monitoring trace levels (e.g., ppm or sub-ppm) of CO, $CO_2$, $H_2O$ (moisture), THC (total hydrocarbon) gases in $N_2$ or He, for example, for specialty chemical manufacturers. Other example applications of the methods and systems of the invention include the monitoring of trace water in fuels, the monitoring of aqueous alcohols, and the monitoring of glucose, lactate, ammonia, and/or glutamine during fermentation processes.

In one aspect, the invention provides a spectroscopic system for detecting electromagnetic radiation that has passed through or is reflected from a sample, the system including an electromagnetic radiation source and a rotatable filter assembly configured to filter a beam of electromagnetic radiation produced by the electromagnetic radiation source, where the assembly includes one or more bandpass optical interference filters, and where the rotatable filter assembly is configured to rotate to provide continuous adjustment of the incident angle of the electromagnetic beam onto the one or more optical interference filters, thereby providing a continuous wavelength sweep in a single wavelength band or multiple wavelength bands. One or more of the bandpass filters is configured such that the surface of the filter is not exactly perpendicular to the electromagnetic beam at any point during the continuous adjustment (e.g., the surface is displaced from perpendicular by up to about 3 degrees, by up to about 5 degrees, by up to about 10 degrees, by up to about 20 degrees, or by up to about 30 degrees). The system also includes a motor coupled to the rotatable filter assembly and an electromagnetic radiation detector configured to detect electromagnetic radiation that has passed through or is reflected from the sample. In certain embodiments, the rotatable filter assembly includes a narrow-band interference filter or plurality of narrow-band interference filters. In certain embodiments, the rotatable filter assembly includes an edge interference filter or plurality of edge interference filters (such as low-pass or high-pass interference filters).

The description of elements of the embodiments of other aspects of the invention can be applied to this aspect of the invention as well.

In another aspect, the invention provides a spectroscopic system for detecting electromagnetic radiation that has passed through or is reflected from a sample including an electromagnetic radiation source; a rotatable filter assembly configured to filter a beam of electromagnetic radiation produced by the electromagnetic radiation source; a motor coupled to the rotatable filter assembly; a position detector including at least one component rigidly attached to the rotatable filter assembly, the position detector is configured to detect an angular position of the rotatable filter assembly; and an electromagnetic radiation detector configured to detect electromagnetic radiation that has passed through or is reflected from a sample.

In certain embodiments, the rotatable filter assembly is configured to rotate about an axis substantially perpendicular to a path of a beam of electromagnetic radiation produced by the electromagnetic radiation source. In certain embodiments, the rotatable filter assembly is configured to rotate about an axis non-perpendicular to a path of a beam of electromagnetic radiation produced by the electromagnetic radiation source at an angle within a range from about 60 degrees to less than 90 degrees (e.g., 89.99 degrees). In certain embodiments, the rotatable filter assembly includes a narrow-band interference filter.

In certain embodiments, the rotatable filter assembly includes a plurality of filters. In certain embodiments, the rotatable filter assembly includes at least three filters.

In certain embodiments, the surface of the filter(s) is parallel to the axis of rotation of the rotatable filter assembly. In certain embodiments, the filter(s) is angularly tilted about an axis perpendicular to the axis of rotation of the rotatable filter assembly and the axis normal to the surface of the filter.

In certain embodiments, the spectroscopic system includes a controller configured to adjust a rotational velocity of the rotatable filter assembly. In certain embodiments, the position detector includes an encoder configured to produce at least a first signal including a series of digital pulses at a first frequency, each digital pulse corresponding to an angular position of the rotatable filter assembly. In certain embodiments, the first frequency is a clock frequency. In certain embodiments, the encoder is configured to produce a second signal, and the spectroscopic system includes an encoder signal processing module configured to combine the first and second signals into a third signal. In certain embodiments, the third signal includes a series of digital pulses having at least double the first frequency. In certain embodiments, the encoder includes an edge detector configured to detect an edge of each of at least two signals produced by the encoder and to thereby produce a signal including a series of digital pulses having at least quadruple the first frequency.

In certain embodiments, the encoder is rigidly attached to the rotatable filter assembly. In certain embodiments, the system includes a speed-reduction mechanism configured to control a velocity of the rotatable filter assembly. In certain embodiments, the speed-reduction mechanism is configured to control the velocity using a digital feedback control.

In certain embodiments, the encoder is configured to produce significantly more digital pulses per rotation of the rotatable filter assembly than are necessary to accurately reproduce an analog signal from the electromagnetic radiation detector. In certain embodiments, the encoder is configured to digitize the analog signal at a frequency greater than a Nyquist criterion corresponding to the analog signal. In certain embodiments, the encoder is configured to digitize the analog signal at a frequency greater than 5 times the Nyquist criterion. In certain embodiments, the encoder is configured to digitize the analog signal at a frequency at least 8 times the Nyquist criterion. In certain embodiments, the encoder is configured to digitize the analog signal at a frequency at least 10 times the Nyquist criterion. In certain embodiments, the encoder is configured to digitize the analog signal with at least 1000 pulses per rotation of the rotatable filter assembly.

In certain embodiments, the spectroscopic system includes a variable gain amplifier configured to convert a light signal from the electromagnetic radiation detector into an electrical signal. In certain embodiments, the variable gain amplifier is in communication with the position detector and is configured to automatically adjust a gain profile of a signal received from the electromagnetic radiation detector based on a detected angular position of the rotatable filter assembly. In certain embodiments, the amplifier is configured to automatically adjust a gain profile of a signal received from the electromagnetic radiation detector based on a magnitude of the signal.

In certain embodiments, the spectroscopic system includes a processor configured to apply a convolution function to a spectral signal from the electromagnetic radiation detector, thereby enhancing wavelength stability and/or repeatability, and/or thereby improving signal-to-noise ratio. In certain embodiments, a width of the convolution function is as great as possible without altering or broadening spectral features of the spectral signal.

In certain embodiments, the spectroscopic system includes a processor configured to apply a baseline correction algorithm to a spectral signal from the electromagnetic radiation detector, thereby enhancing long-term measurement stability.

In certain embodiments, the spectroscopic system includes a plurality of electromagnetic radiation sources, thereby enabling detection of electromagnetic radiation over a broader spectrum and/or over multiple spectra. In certain embodiments, the plurality of electromagnetic radiation sources includes a UV radiation source and an IR radiation source. In certain embodiments, the spectroscopic system includes an analog-to-digital acquisition mechanism in communication with the electromagnetic radiation detector and the position detector, where the analog-to-digital acquisition mechanism is configured to digitize, store, and/or process data corresponding to the detected electromagnetic radiation. The spectroscopic system may include a computer or may otherwise share input and output with a computer 2802 (e.g., a computer internal or external to the spectroscopic system), the computer including software for digitizing, receiving, storing, and or processing data corresponding to the detected electromagnetic radiation and/or signals created by such detected electromagnetic radiation as illustrated in FIG. 28. The computer may also include a keyboard or other portal for user input, and a screen for display of data to the user. The computer may include software for process control, data acquisition, data processing, and/or output representation. The spectroscopic system may include a wireless system for acquisition of data and/or system control. For example, the wireless system may allow wireless data transfer from and/or to a computer, allowing wireless input and/or output (and/or system control) by/to a user via a user interface connected to the computer, such as a keyboard and/or display screen. The spectroscopic system may also include a battery system configured to enable stand-alone operation capability.

The description of elements of the embodiments of other aspects of the invention can be applied to this aspect of the invention as well.

In another aspect, the invention provides a spectroscopic system for detecting electromagnetic radiation that has passed through or is reflected from a sample, including an electromagnetic radiation source; a rotatable filter assembly configured to filter a beam of electromagnetic radiation produced by the electromagnetic radiation source; a motor coupled to the rotatable filter assembly, an electromagnetic radiation detector configured to detect electromagnetic radiation that has passed through or is reflected from a sample and to output a corresponding analog spectral signal; and a position detector configured to detect an angular position of the rotatable filter assembly, the position detector including an encoder configured to produce at least a first signal including a series of digital pulses at a first frequency, each digital pulse corresponding to an angular position of the rotatable filter assembly, wherein the encoder is configured to produce significantly more digital pulses per rotation of the rotatable filter assembly than are necessary to reproduce the analog spectral signal.

In certain embodiments, the encoder is configured to digitize the analog signal at a frequency greater than a Nyquist criterion corresponding to the analog signal. In certain embodiments, the encoder is configured to digitize the analog signal at a frequency greater than 5 times the Nyquist criterion. In certain embodiments, the encoder is configured to digitize the analog signal at a frequency at least 8 times the Nyquist criterion. In certain embodiments, the encoder is configured to digitize the analog signal at a frequency at least 10 times the Nyquist criterion. In certain embodiments, the encoder is configured to digitize the analog signal with at least 1000 pulses per rotation of the rotatable filter assembly.

The description of elements of the embodiments of other aspects of the invention can be applied to this aspect of the invention as well.

In another aspect, the invention provides a spectroscopic system for detecting electromagnetic radiation that has passed through or is reflected from a sample, including an electromagnetic radiation source having a variable intensity; a filter assembly configured to filter a beam of electromagnetic radiation produced by the electromagnetic radiation source; a position detector configured to detect a position of the filter assembly; a controller configured to adjust the intensity of the electromagnetic radiation source; and an electromagnetic radiation detector configured to detect electromagnetic radiation that has passed through or is reflected from a sample.

In certain embodiments, the filter assembly is rotatable and the position detector is configured to detect an angular position of the filter assembly.

In certain embodiments, the controller is in communication with the position detector and is configured to adjust the intensity of the electromagnetic radiation source based on a detected position of the filter assembly. In certain embodiments, the filter assembly includes a filter having an active portion and an inactive portion and the controller is configured to decrease the intensity of the electromagnetic radiation source when a beam of electromagnetic radiation from the electromagnetic radiation source is incident on an inactive portion of the filter.

In certain embodiments, the controller includes a voltage regulator for controlling a voltage supplied to the electromagnetic radiation source.

In certain embodiments, the spectroscopic system includes a plurality of electromagnetic radiation sources. In certain embodiments, the spectroscopic system includes a plurality of electromagnetic radiation detectors.

In certain embodiments, the spectroscopic system includes a variable gain amplifier configured to convert a light signal from the electromagnetic radiation detector into an electrical signal. In certain embodiments, the amplifier is in communication with the position detector and is configured to automatically adjust a gain profile of the electrical signal based on a detected position of the filter assembly.

In certain embodiments, the filter assembly is configured for rotation about an axis substantially perpendicular to a path of a beam of electromagnetic radiation produced by the electromagnetic radiation source.

The description of elements of the embodiments of other aspects of the invention can be applied to this aspect of the invention as well.

In another aspect, the invention provides a spectroscopic system for monitoring electromagnetic radiation that has passed through or is reflected from a sample including an electromagnetic radiation source; a filter assembly configured to filter a beam of electromagnetic radiation produced by the electromagnetic radiation source; an electromagnetic radiation detector configured to detect electromagnetic radiation that has passed through or is reflected from a sample; and a processor in communication with the electromagnetic radiation detector, the processor configured to: (i) apply a first calibration spectrum to a first recorded spectrum obtained from the electromagnetic radiation detector, thereby determining a measure of one or more compounds in the sample; and (ii) modify the first calibration spectrum to account for a baseline variation of recorded spectra over time using at least a second, subsequent recorded spectrum obtained from the electromagnetic radiation detector.

The description of elements of the embodiments of other aspects of the invention can be applied to this aspect of the invention as well.

In another aspect, the invention provides a system for monitoring a process including an electromagnetic radiation source; a filter assembly configured to filter a beam of electromagnetic radiation produced by the electromagnetic radiation source; a sampling mechanism configured to alternately direct a sample from a first stream associated with the monitored process into a sampling area and direct a sample from a second stream associated with the monitored process into the sampling area; an electromagnetic radiation source configured to direct an electromagnetic radiation beam from the electromagnetic radiation source to the sampling area; an electromagnetic radiation detector configured to detect electromagnetic radiation that has passed through or is reflected from the sampling area; and a processor configured to: (i) obtain a first spectrum corresponding to the first stream; (ii) store the first spectrum as a baseline spectrum; and (iii) obtain a second spectrum from the second stream using the baseline spectrum, wherein the second spectrum reflects a compositional difference between the first and second streams.

In certain embodiments, the sampling mechanism includes a solenoid valve for switching between the first and second streams. In certain embodiments, the first stream is an input stream to the monitored process and the second stream is an output stream from the monitored process. In certain embodiments, the first stream is an output stream from the monitored process and the second stream is an input stream to the monitored process.

The description of elements of the embodiments of other aspects of the invention can be applied to this aspect of the invention as well.

In another aspect, the invention provides a spectroscopic method for detecting electromagnetic radiation that has passed through or is reflected from a sample, including: filtering a beam from an electromagnetic radiation source with a rotating filter assembly; detecting an angular position of the rotating filter assembly with a position detector having at least one component rigidly coupled to the rotating filter assembly; intercepting the beam with a sample; detecting the beam with an electromagnetic radiation detector; and processing a spectral data signal from the electromagnetic radiation detector to produce chemical information about the sample.

In certain embodiments, the rotating filter assembly is configured to rotate about an axis substantially perpendicular to a path of a beam of electromagnetic radiation produced by the electromagnetic radiation source. In certain embodiments, the rotating filter assembly includes a narrow-band interference filter. In certain embodiments, the rotating filter assembly includes at least three filters.

In certain embodiments, the position detector includes an encoder configured to produce at least a first signal comprising a series of digital pulses at a first frequency, each digital pulse corresponding to an angular position of the rotating filter assembly.

In certain embodiments, the method includes digitizing an analog spectral signal from the electromagnetic radiation detector is performed. In certain embodiments, digitizing is performed at a frequency significantly greater than necessary to accurately reproduce the analog spectral signal; digitizing is performed at a frequency greater than a Nyquist criterion corresponding to the analog spectral signal; and/or digitizing is performed at a frequency greater than at least ten times the Nyquist criterion.

In certain embodiments, a step of applying a convolution function to a spectral signal from the electromagnetic radiation detector is performed to enhance wavelength stability and/or repeatability, and/or to improve signal-to-noise ratio.

The description of elements of the embodiments of other aspects of the invention can be applied to this aspect of the invention as well.

In yet another aspect, the invention provides a spectroscopic method for detecting electromagnetic radiation that has passed through or is reflected from a sample to produce chemical information about the sample, the method including: filtering a beam from an electromagnetic radiation source with a rotating filter assembly; intercepting the beam with a sample; detecting the beam with an electromagnetic radiation detector configured to output an analog spectral signal; detecting an angular position of the rotating filter assembly with a position detector, the position detector comprising an encoder configured to produce at least a first signal comprising a series of digital pulses at a first frequency, each digital pulse corresponding to an angular position of the rotating filter assembly, wherein the encoder is configured to produce significantly more digital pulses per rotation of the rotating filter assembly than are necessary to reproduce the analog spectral signal; digitizing the analog spectral signal using the first frequency as a clock frequency; and processing the digitized analog spectral signal to produce chemical information about the sample.

In certain embodiments, the first frequency is greater than a Nyquist criterion corresponding to the analog spectral signal. In certain embodiments, the first frequency corresponds to at least 1000 pulses per rotation of the rotating filter assembly (or, alternatively, at least 2000, 1500, 1250, 900, 800, 700, 600, or 500 pulses per rotation).

The description of elements of the embodiments of other aspects of the invention can be applied to this aspect of the invention as well.

In yet another aspect, the invention provides a spectroscopic method for detecting electromagnetic radiation that has passed through or is reflected from a sample to produce chemical information about the sample, including: filtering a beam from an electromagnetic radiation source with a filter assembly, the electromagnetic radiation source having a variable intensity; intercepting the beam with a sample; detecting the beam with an electromagnetic radiation detector; detecting a position of the filter assembly with a position detector; adjusting the intensity of the electromagnetic radiation source; and processing spectral data from the electromagnetic radiation detector to produce chemical information about the sample.

In certain embodiments, adjusting the intensity of the electromagnetic radiation source is based on a detected position of the filter assembly.

The description of elements of the embodiments of other aspects of the invention can be applied to this aspect of the invention as well.

In yet another aspect, the invention provides a spectroscopic method for monitoring electromagnetic radiation that has passed through or is reflected from a sample, the method including: filtering a beam from an electromagnetic radiation source with a filter assembly; intercepting the beam with a sample; detecting the beam with an electromagnetic radiation detector; applying a first calibration spectrum to a first recorded spectrum obtained from the electromagnetic radiation detector, thereby determining a measure of one or more compounds in the sample; and modifying the first calibration spectrum to account for baseline variation of the recorded spectra over time using at least a second, subsequent recorded spectrum obtained from the electromagnetic radiation detector.

The description of elements of the embodiments of other aspects of the invention can be applied to this aspect of the invention as well.

In yet another aspect, the invention provides a spectroscopic method for monitoring a process, including: directing a first sample from a first stream associated with the monitored process into a sampling area; directing a second sample from a second stream associated with the monitored process into the sampling area; detecting filtered radiation that has passed through or is reflected from the sampling area; determining a first spectrum corresponding to the first stream; storing the first spectrum as a baseline spectrum; and determining a second spectrum from the second stream using the baseline spectrum, wherein the second spectrum reflects a compositional difference between the first and second streams.

In certain embodiments, the first stream is an input stream to the monitored process and the second stream is an output stream to the monitored process. In certain embodiments, the first stream is an output stream to the monitored process and the second stream is an input stream to the monitored process.

The description of elements of the embodiments of other aspects of the invention can be applied to this aspect of the invention as well.

In yet another aspect, the invention provides a method for increasing the robustness and/or stability of the measurement, including: obtaining a first spectrum from an electromagnetic radiation detector; applying a classical least squares analysis to the first spectrum using a principal calibration matrix to obtain detection values; determining a residual magnitude by quantifying how well the first spectrum fit the principal calibration matrix; comparing the residual magnitude to a predetermined threshold to determine if a threshold condition exists and, if a threshold condition exists, creating a secondary reference matrix using the first spectrum if a secondary reference matrix does not exist and, if the secondary reference matrix exists, adding the first spectrum to the secondary reference matrix as a row or a column; adding the rows or columns of the secondary reference matrix to the principal reference matrix to update the reference matrix; and reapplying a classical least squares analysis to a second spectrum from an electromagnetic radiation detector.

In certain embodiments, the size of the secondary reference matrix is predetermined. In certain embodiments, determining a residual magnitude comprises computing a mean of an absolute function of a classical least squares fit of the first spectrum; and/or determining a residual magnitude comprises computing a maximum value of an absolute function of a classical least squares fit of the first spectrum.

In certain embodiments, the threshold condition exists when the residual magnitude exceeds a predetermined threshold value; the threshold condition exists when the first spectrum is substantially orthogonal to the principal calibration matrix; the reference matrix comprises spectral data from a beam of electromagnetic radiation that has not passed through a sample; the principal calibration matrix comprises spectrum values corresponding only to substances to be detected; and/or the principal calibration matrix comprises spectrum values corresponding to substances to be detected and other substances likely to be found together with the substances to be detected.

The description of elements of the embodiments of other aspects of the invention can be applied to this aspect of the invention as well.

BRIEF DESCRIPTION OF DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

It is contemplated that methods, systems, and processes described herein encompass variations and adaptations developed using information from the embodiments described herein.

Throughout the description, where systems and compositions are described as having, including, or comprising specific components, or where processes and methods are described as having, including, or comprising specific steps, it is contemplated that, additionally, there are systems and compositions of the present invention that consist essentially of, or consist of, the recited components, and that there are processes and methods of the present invention that consist essentially of, or consist of, the recited processing steps.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are used herein to aid the reader and are not meant to limit the interpretation of the subject matter described.

Figure 1:
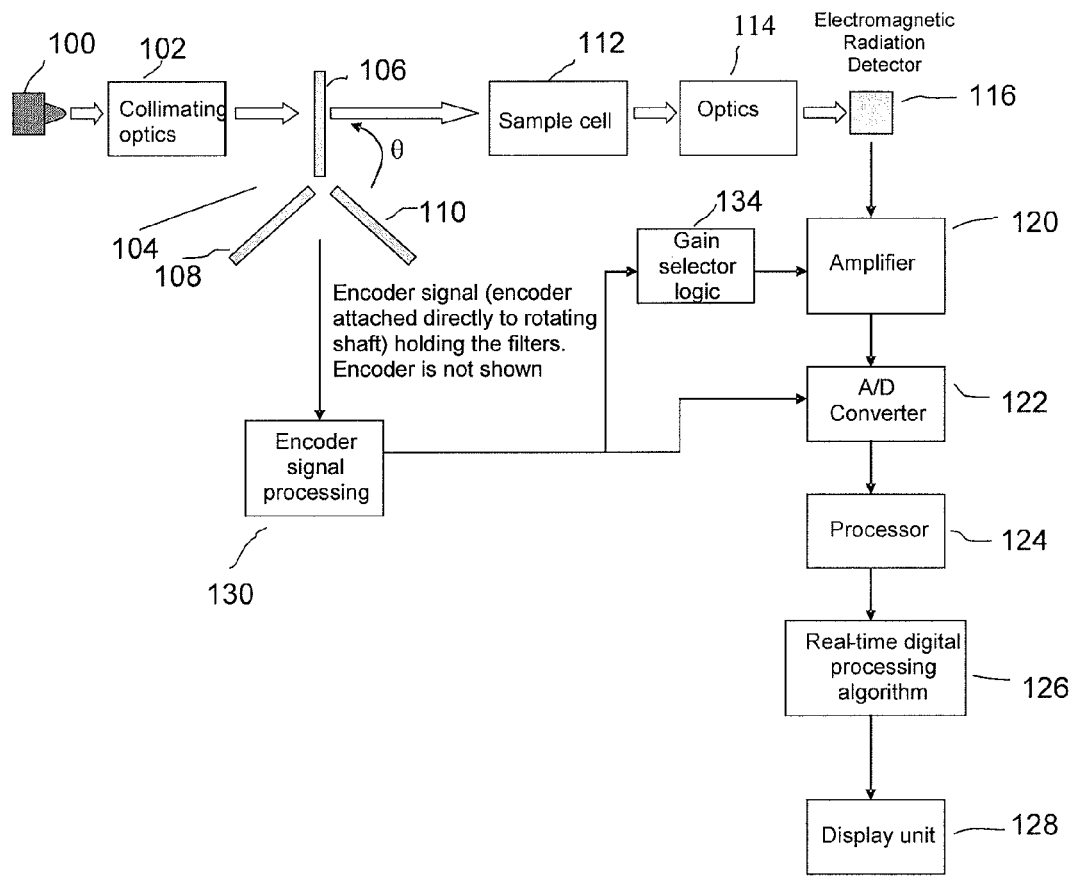
FIG. 1 is a block diagram of a spectroscopic system for detecting radiation according to an illustrative embodiment of the present invention.

FIG. 1 is a block diagram of a spectroscopic system for detecting electromagnetic (EM) radiation according to an embodiment of the present invention. An EM radiation source 100, or multiple EM radiation sources 100 covering one or multiple wavelength regions, are configured to direct a beam of EM radiation to a filter assembly 104 (as shown, having three filters). The EM radiation source 100 may be made out of a heated filament, LED type, or any other suitable type. The beam may be collected and collimated by collimating optics 102, which may be made out of a series of lenses or mirrors. The collimated beam is intercepted by the filter assembly 104, which is shown as viewed from the top.

In certain embodiments, the filter assembly 104 is configured for rotation. The filter assembly 104 may be positioned relative to the collimated beam from the light source 100 such that the axis of rotation is substantially perpendicular to the path of the beam. Alternatively, the axis of rotation may be fixed such that it is not perpendicular to the path of the beam, in order to reduce or eliminate back-reflected light and/or stray light and/or to further control the wavelength coverage.

In certain embodiments, the filter assembly 104 may have at least three filters (106, 108, 110). Each of the filters may be a narrow-band interference filter configured to pass a certain narrowband of the EM radiation incident on it. These individual filters are generally available commercially off-the-shelf. The filter assembly 104 may be configured as indicated in FIG. 1 such that the angle (A) between the collimated beam and a filter varies. In addition, rotation causes the beam to be incident on the different filters (106, 108, 110) in the assembly. The numbers of filters that can be employed is between one and four, depending on the measurement or monitoring application. In particular, this depends on the number of compounds that need to be measured or monitored. The transmission wavelength of each of the filters can generally be tuned from its original wavelength to approximately 95% of the original wavelength assuming a maximum of 40-degree change in the incident angle. For example, a filter that has a nominal (at 90-degree incident angle) transmission wavelength peak at 2000 nm can be tuned to approximately 1900 nm (0.95×2000 nm). If the target compounds happen to have spectral features within this region (1900 nm-2000 nm), using only this filter is sufficient for the measurement. Multiple filters are needed for a wider spectral coverage. Multiple filters may also be used to provide spectral coverage of distinct wavelength regions, i.e. regions that are not close to each other on the wavelength scale. For example, one filter may have a nominal transmission at 2000 nm and the other at 8000 nm. Continuing on the beam path in FIG. 1, the filtered beam then passes through a sample cell 112, which may contain a sample. The sample may be gaseous, liquid or solid. Additional optics 114, such as focusing, collimating and/or collecting optical elements, may be used to increase the EM radiation throughput or to better manage or direct the EM radiation when necessary. In the sample cell 112, the beam is intercepted by the sample, which modifies the spectrum of the original beam. The interaction may be in the form of absorption, fluorescence or other types of light-matter interactions. The beam may be then focused onto an EM radiation detector 116 using focusing optics 114. The EM radiation detector 116 may be a semiconductor based detector such as silicon photodiode, a pyroelectric photo-detector, or other types of EM radiation detectors. Using an amplifier 120, a spectral signal from the EM radiation detector 116 may be turned into an electrical signal, and may then be converted into a digital signal by an analog-to-digital (A/D) converter 122.

In certain embodiments, the surface of the filter(s) is parallel to the axis of the rotation or the rotatable filter assembly. With this configuration, the angular coverage of the rotating filter spectrometer starts from zero incident angle. For example, if a narrow-band filter has a nominal (zero angle) peak transmission at 2000 nm, the starting wavelength of the spectral coverage of the spectrometer with the surface of filter parallel to the axis of the rotation is theoretically 2000 nm.

Figure 24:
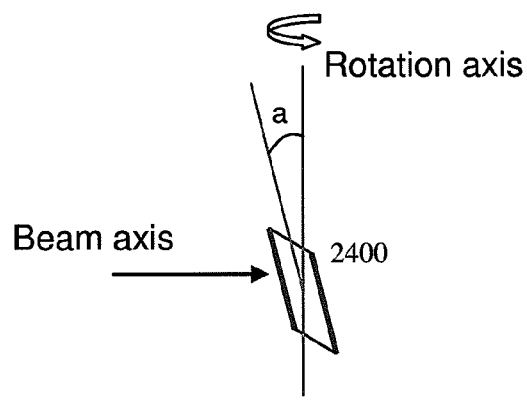
FIG. 24 is an illustration of tilted filter, tilted with respect to the rotation axis, according to an illustrative embodiment of the present invention.
Figure 26:
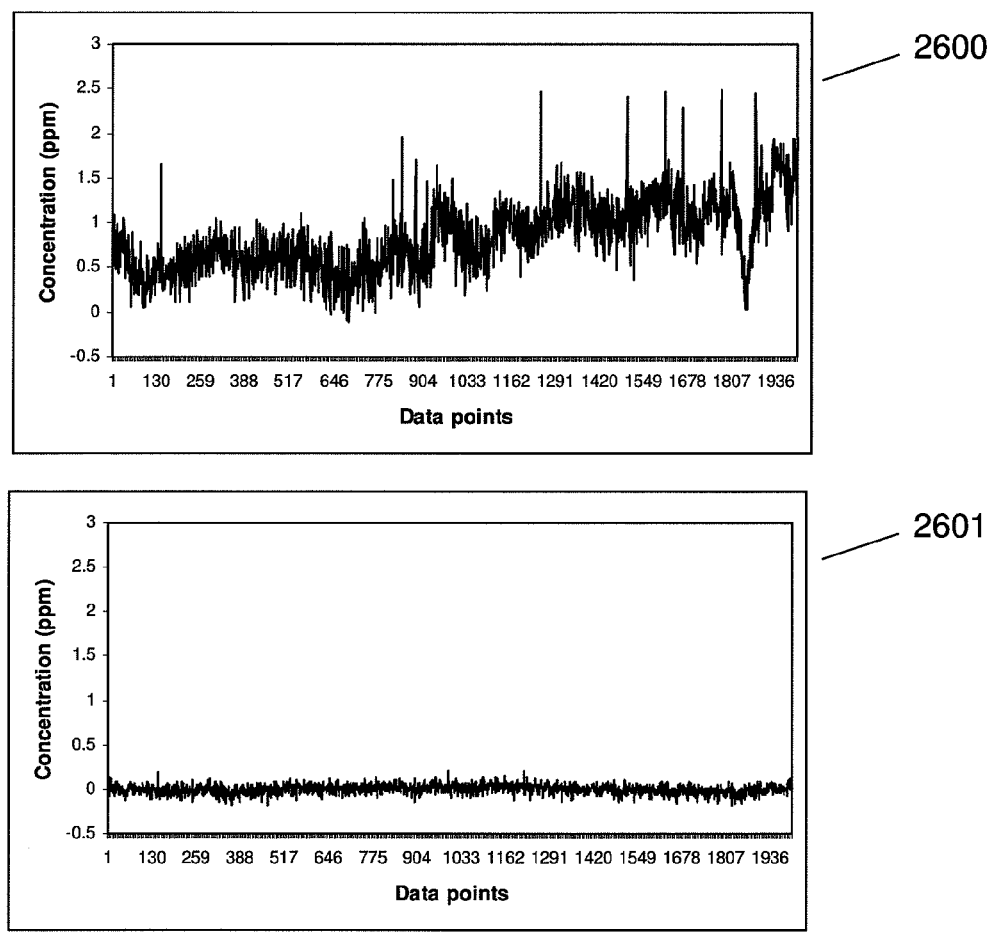
FIG. 26 is a comparison of measurement stability between (i) system with rotation axis perpendicular to the beam and (ii) system with rotation axis non-perpendicular to the beam, according to an illustrative embodiment of the present invention.

In certain embodiment, the surface of one, some, or all of the filters 2400 (FIG. 24) is angularly tilted about an axis perpendicular to the axis of rotation of the rotatable filter assembly and the axis normal to the surface of the filter. It is found that tilting of the filter(s) eliminates or suppresses the back-reflected light or stray light that may cause measurement inaccuracy, non-linearity and/or instability and results in a significant advantage in measurement stability. FIG. 26 shows a comparison between the measurement stability of a system having the rotation axis perpendicular to the electromagnetic beam (2600) and the measurement stability of a system having the rotation axis at 87 degrees to the electromagnetic beam (2601). Each plot corresponds to a 72-hour of zero stability run, specifically, the system was configured and calibrated for moisture analysis at around 2.7 µm, and the sample gas was dry nitrogen. Both systems employed a least-squares regression chemometric method to predict the moisture concentration upon a moisture calibration spectrum. Plots 2600 and 2601 demonstrate the significant advantage in measurement stability afforded by tilting the filter(s) in this way.

Figure 27:
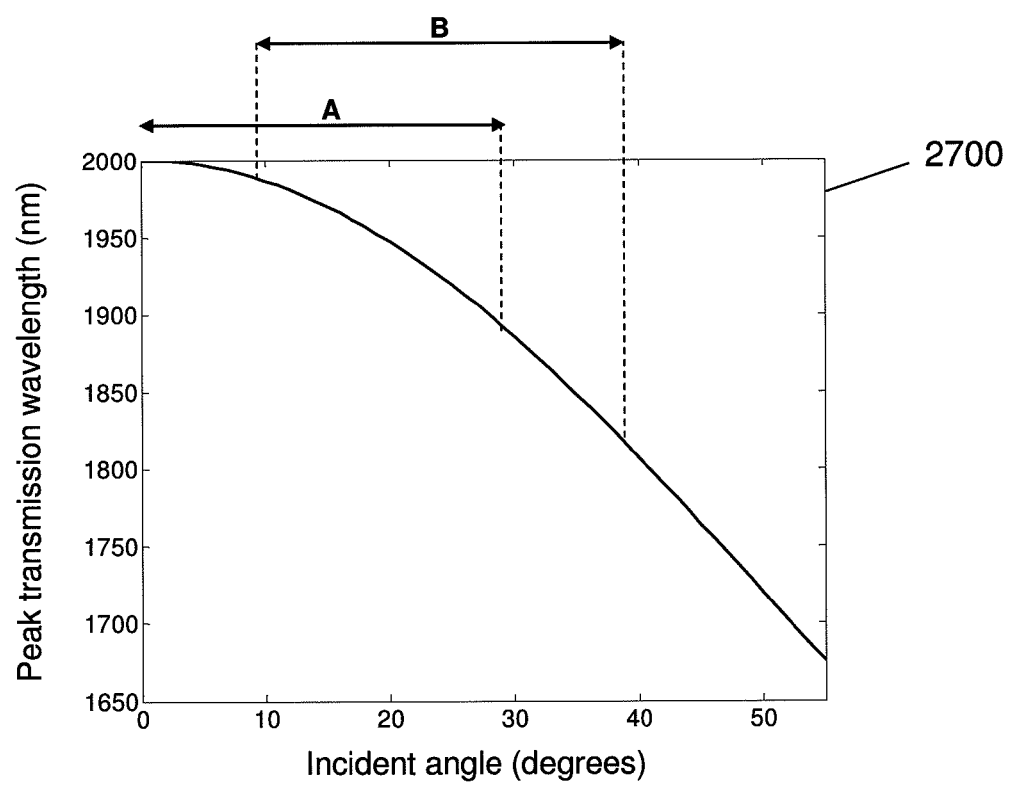
FIG. 27 is a graph illustrating the relationship of peak transmission wavelength of a bandpass interference filter with the incident angle.

It is also found that tilting of the filter(s) improves control of the wavelength coverage of the spectrometer, in light of certain filter characteristics and mechanical angular coverage of the rotatable filter assembly. For purposes of illustration, and without wishing to be bound by any particular theory, FIG. 27 shows the theoretical relationship between the incident angle and the peak transmission wavelength of a narrow-band interference filter with a nominal (zero-angle) peak wavelength of 2000 nm. Configuration "A" illustrates a system with the surface of the filter parallel to the axis of rotation. Assuming that the effective angular coverage from the rotating filter assembly is 0-30 degrees, the resulting spectral coverage is approximately 2000 nm-1900 nm. On the other hand, in configuration "B", in which the surface of the filter is tilted at 10 degrees with respect to the rotation axis, the resulting incident angle coverage with 0-30 degrees rotation is between 10-40 degrees, resulting in a spectral coverage of approximately 1980 nm-1830 nm, as illustrated in FIG. 27.

In some embodiments, the amplifier 120 is a fixed gain amplifier. Alternatively, the amplifier 120 may have a variable gain.

A digital spectral signal from the A/D converter 122 may be fed to a processor 124 in which a real-time digital signal processing algorithm 126 is applied. The final outcome of the process may be quantitative chemical composition data, which may be displayed in a display unit 128.

The use of multiple filters such as shown in FIG. 1 (as shown, filters 106, 108, and 110) enables wide discrete spectral coverage. For example, one filter may cover the near infrared region around 2000 nm, and the others may cover the mid-infrared region around 8000 nm. The EM radiation detector 116 and the EM radiation source 100 may produce a signal at extremely different magnitudes in the different spectral regions. For example, when using an amplifier 120 with a fixed gain, a signal from the 8000 nm may amount to 1 volt, whereas a signal from the 2000 nm may amount to 1000 volts due to the higher EM radiation source output and better detector responsivity at the near infrared region.

In certain embodiments, an amplifier 120 switches the gain based upon an angular position of the filters as commanded by the gain selector logic 134. In another embodiment, an amplifier 120 switches the gain based upon the magnitude of a spectral signal itself.

The A/D convertor 122 receives its timing or clock signal from an encoder 208 that is preferably attached rigidly to the filter assembly 104. The encoder 208 may produce digital pulses that correspond to an angular position of the filter assembly 104.

Figure 2:
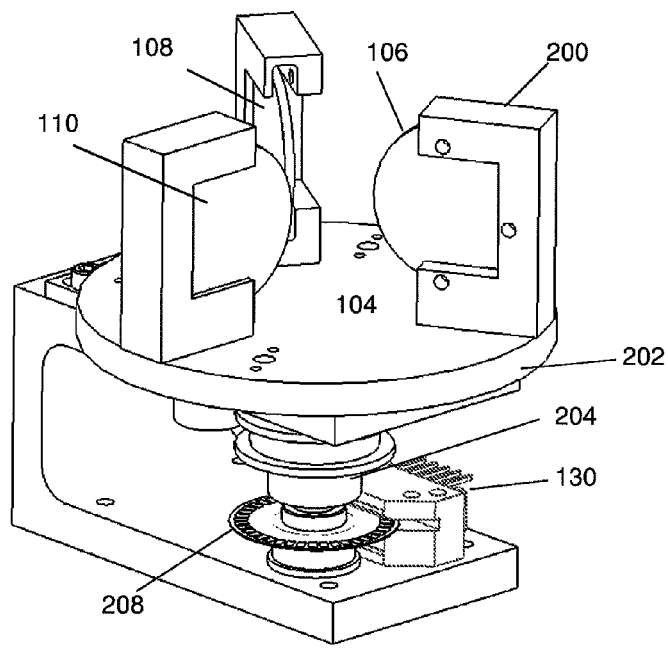
FIG. 2 is a perspective view of a rotating filter assembly, according to an illustrative embodiment of the invention.

FIG. 2 shows an encoder 208 in more detail. The encoder 208 may include an encoder electronics unit 206 for carrying the digital pulses corresponding to an angular position of a rotating filter assembly 104. An example of such an off-the-shelf encoder is EM-1-1250 made by US Digital (Vancouver, Wash.), which produces 1250 pulses per quadrature channel per rotation.

Figure 3:
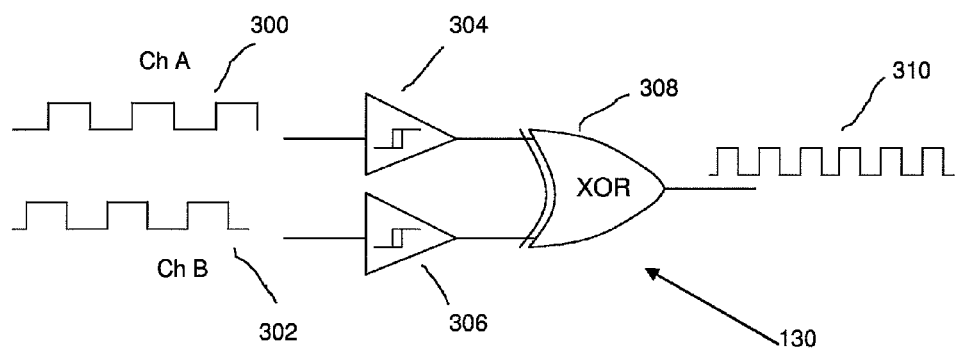
FIG. 3 is schematic of an encoder signal processing circuit, according to an illustrative embodiment of the invention.

The encoder pulses may be sent to an encoder signal processing unit 130, of which a simplified schematic of one embodiment is shown in FIG. 3. An encoder signal processing unit 130 may include two Schmitt triggers (304, 306) that reject any glitches or noise due to electromagnetic interference. The clean digital pulses may then be sent to an XOR gate 308 to combine the two quadrature signals (300, 302) from an encoder into a single signal 310 that is doubled in frequency.

For example, in some embodiments, an encoder 208 produces 1250 quadrature pulses per rotation. Upon exiting the encoder signal processing unit 130, the signal 310 has a frequency at least double the frequency of one of the quadrature signals (300, 302) to become at least 2500 pulses per rotation. The encoder signal processing unit 130 enables greater over-sampling and data averaging that thereby improves wavelength stability and the system's signal-to-noise ratio.

Figure 23:
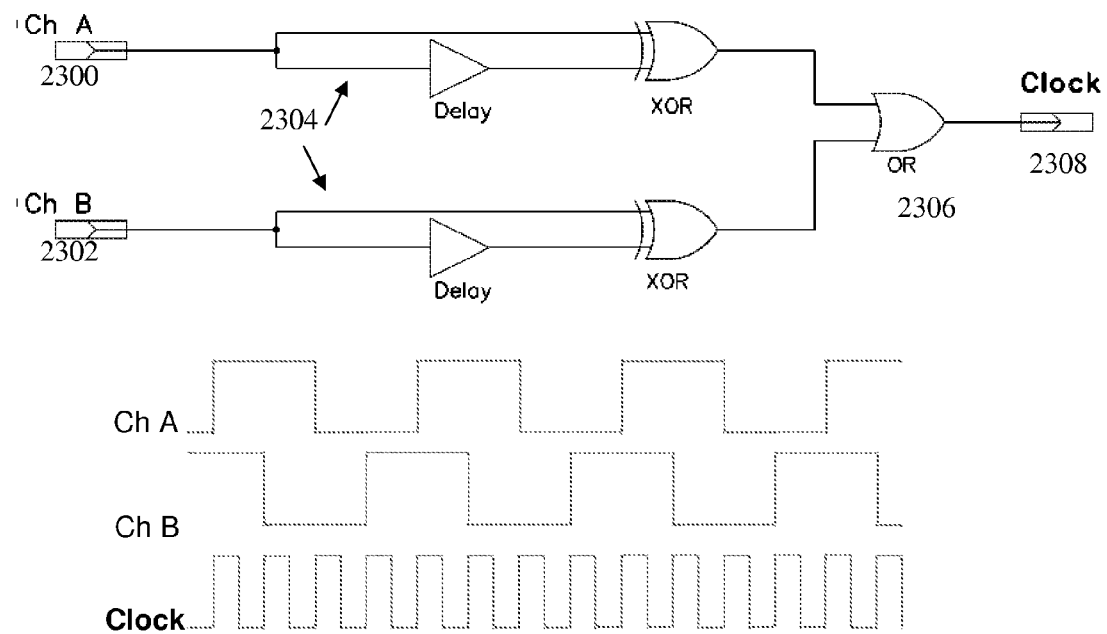
FIG. 23 is an illustration of a method for quadrupling a clock signal from an encoder according to an illustrative embodiment of the present invention.

In certain embodiments, the pulses are multiplied further in frequency by employing a different electronics scheme. For example, to quadruple an original clock frequency, the following scheme may be used. As shown in FIG. 23, an edge detector 2304 may be used to trigger a short pulse by detecting either a positive or negative edge in the incoming signals from a first and second channel (2300, 2302). The signals from the first and second channels (2300, 2302) are sent to the edge detector 2304 and then the same signal is delayed to create the effect of a difference, which will be seen by the edge detector 2304 as a reason to output a high logic. The high state may last the duration of the delay introduced. The duration of the pulse may be long enough to allow an A/D convertor 122 to perform a conversion. Illustrated in FIG. 23 is an implementation of this using logic gates. Other methods include the use of multiple combinations of logic gates, flip-flops, logic gates and passive components, and analog components to achieve similar purpose. The delay can be implemented using multiple gates which are intended to increase the pulse width out of the edge detector.

With reference to FIG. 3, at least one component of an encoder 208 may be rigidly attached to a filter assembly 104. This may help to ensure that there is no mechanical compliance (or "play") between the two elements, thus providing for a more stable and repeatable timing or clock signal position regardless of variations in environmental conditions, such as vibration and temperature variations. Such an arrangement may also enable the use of a speed reduction mechanism, such as gear or belt drives, to optimize power transmission while maintaining repeatable and stable clock signal positions.

The filter assembly 104 may include a table 202 for mounting filters (as shown in FIGS. 2, 106, 108, and 110). Each filter may be secured to the table 202 with a mounting bracket 200. The table 202 may be coupled to a shaft 204.

In certain embodiments, a speed-reduction mechanism may be coupled to the motor that drives the filter assembly 104. A speed-reduction mechanism may be a belt-and-pulley type, which may provide smooth, noise-free motion. In certain embodiments, the velocity of the rotating filter assembly 104 is adjusted and controlled using a digital feedback control.

To further improve wavelength stability/repeatability, the measured signal just before the A/D conversion is over-sampled, i.e. the signal is digitized at a frequency significantly higher than the Nyquist criterion which is required to accurately reproduce the analog signal digitally. Such over-sampling is achieved by employing an encoder that provides a large number of pulses per rotation. To illustrate by example, if the to-be-measure spectral features require a clock signal of 100 pulses per rotation, the encoder 208 should be designed or chosen such that it provides significantly more than 100 pulses per rotation. A suitable encoder for this example is one that provides on the order of 1000 pulses per rotation. The upper limit would be the maximum allowable sampling frequency of the A/D converter 122.

Figure 4:
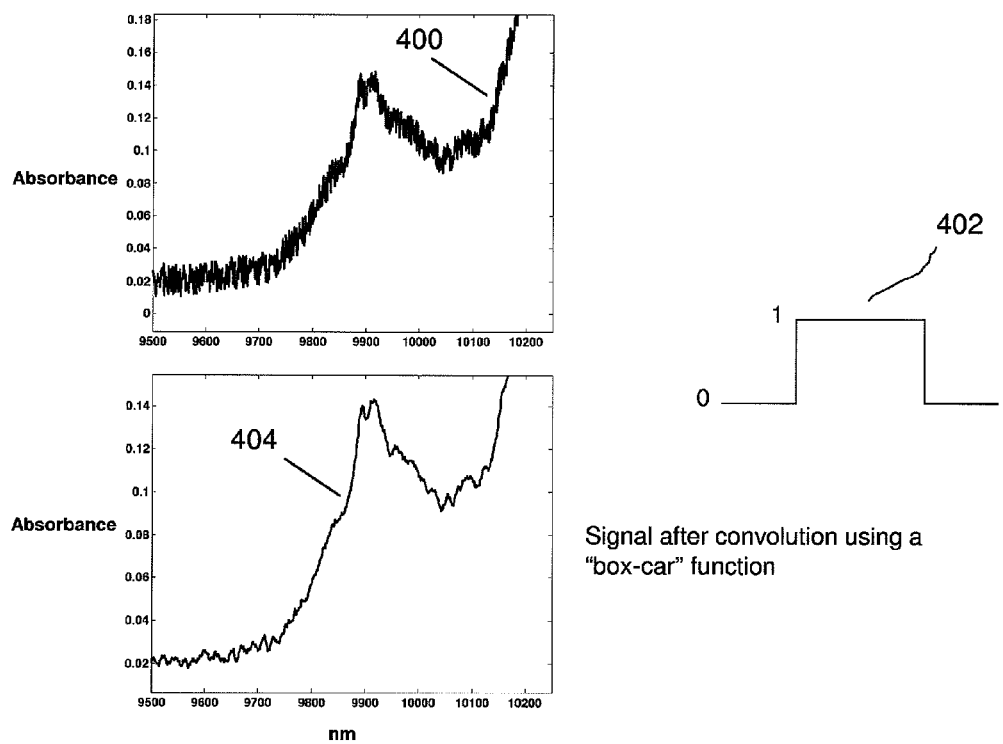
FIG. 4 is an illustration of signal-to-noise ratio improvement after application of a convolution function to a spectral signal, according to an illustrative embodiment of the invention.

This signal over-sampling may be combined with a digital convolution step performed in the processor 124. The combination of data over-sampling and convolution would improve the wavelength stability or repeatability and the spectral signal-to-noise ratio. The convolving function 402 may be a "boxcar" function, triangular function, Gaussian function or other applicable functions. For the purpose of wavelength stability improvement, the exact type of convolving function 402 is less important than the width of the function. The width of the convolving function 402 should be maximized to the point where widening it further would alter or broaden the actual spectral features of the measured compound. For example, FIG. 4 shows a "box-car" convolution function 402 applied to a raw signal 400. It can be seen that the convoluted signal 404 is shown with an improved signal-to-noise ratio without loss of any of the relevant spectral features.

Figure 5:
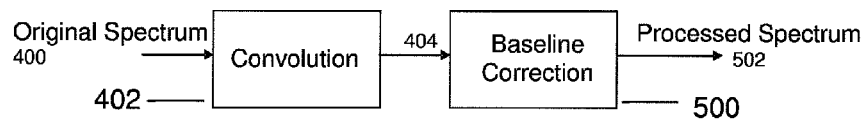
FIG. 5 is a block diagram of a spectroscopic method according to an illustrative embodiment of the present invention.

A common source of measurement instability is baseline instabilities of the recorded spectrum, which may be due to slight optical alignment changes (for example due to temperature variations), light source degradation, dirty optics, etc. FIG. 5 shows a block diagram schematic of a spectral processing method using a baseline correction algorithm to produce a processed spectrum 502. A baseline correction algorithm 500 may be employed to ensure long-term measurement stability. In one embodiment, a polynomial fit is applied to the spectrum A linear or a second order fit is generally sufficient to remove common types of baseline variations, although a higher order fit may also be used as long as it does not remove the relevant spectral features. In another embodiment, a spectral differentiation is used to remove the baseline variations. The spectral differentiation algorithm is of the form S_new(n)=S(n+1)−S(n), or variations thereof, where S_new is the resulting baseline-corrected spectrum, S is the original spectrum, and n is the data element of the spectrum.

Figure 6:
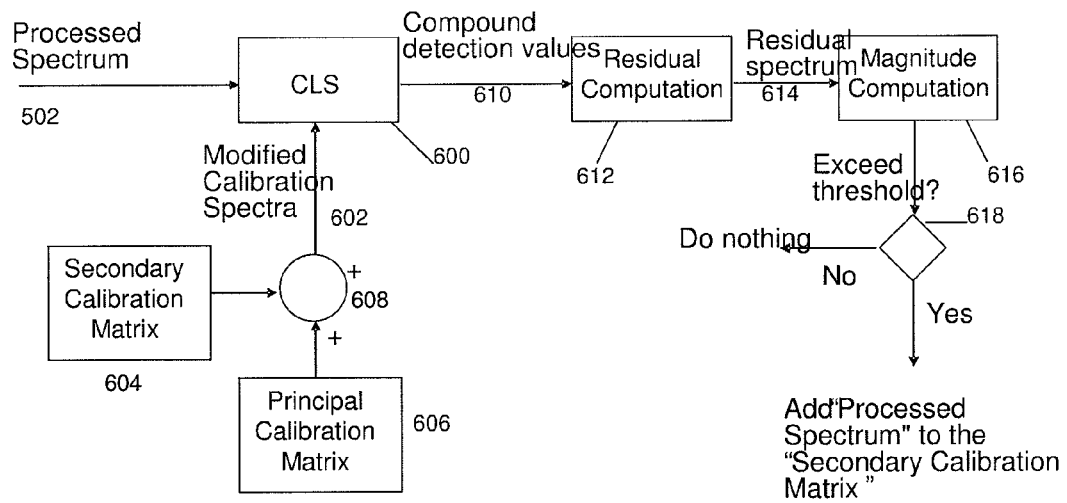
FIG. 6 is a flow chart of a spectral processing method using an adaptive algorithm according to an illustrative embodiment of the present invention.

As shown in one embodiment, shown in FIG. 6, to produce the actual measurement values, i.e. the compounds' concentration or density values, a classical least squares analysis 600 is applied to the processed spectrum 502. With this method, a calibration spectra (the "K" matrix) 602, described below, is needed before hand. This matrix contains the calibration spectra of all of the target compounds (compounds to be measured).

In continuous monitoring applications in which the instrument cannot be re-zeroed ("zero" or background spectrum taken) frequently, there may be baseline variations that cannot be completely fitted by a polynomial function. This is particularly true with a filter-based spectroscopy system of the present invention, which tends to be more susceptible to these type of baseline errors due to the nonlinear wavelength-angle function. In addition, spectral variations that are due to un-modeled interferences such as those due to other unknown compounds may also be present, which would also cause measurement instabilities.

In one embodiment, shown in FIG. 6, the present invention overcomes these problems as described below. An adaptive algorithm is designed; one that continuously and automatically modifies the calibration spectra ("K" matrix) to account for any un-modeled spectral variation including those associated with long-term drifts or instabilities. FIG. 6 shows a flow chart of this algorithm showing its basic operation. The processed spectrum (raw spectrum upon passing through convolution and linear baseline correction) is fitted with a calibration matrix containing the original or the principal calibration matrix (calibration spectra of the target compounds) 606 and a secondary calibration matrix 604. A secondary calibration spectrum is added to the secondary calibration matrix each time the magnitude of the residual spectrum from the CLS analysis exceeds a certain predetermined threshold value, as indicated by a decision step 618 in the flow chart. The rows or columns of the secondary calibration matrix 604 are added 608 to the rows or columns of the principal calibration matrix 606 to obtain a modified calibration spectra or "K" matrix 602.

To illustrate by means of an example, consider a principal calibration matrix containing three target compounds: $k_A(\lambda)$ for target compound A, $k_B(\lambda)$ for target compound B, and $k_C(\lambda)$ for target compound C, where $k(\lambda)$ is essentially a spectrum of the target compound calibrated at a certain compound concentration or density value. When a disturbance occurs such that the measured spectrum could not be adequately modeled by the principal calibration matrix (as quantified by the residual magnitude or spectrum 614, determined by employing the step of residual computation 612), the measured spectrum $s_n(\lambda)$ is added to the calibration matrix. Thus, the calibration matrix 602 becomes:

$$\begin{pmatrix} k_A(\lambda) \\ k_B(\lambda) \\ k_C(\lambda) \\ s_n(\lambda) \end{pmatrix} \leftarrow \text{Secondary calibration spectrum}$$

where n=1, 2, 3, . . .

There is more than one approach to compute the residual magnitude 616 from the residual spectrum. For example, in one embodiment, the magnitude computation of the residual spectrum involves computing the mean value of the absolute function of the residual spectrum. Other magnitude computation method may be used, such as calculating the maximum value of the absolute function of the residual spectrum.

In certain embodiments, the size of the secondary calibration matrix 604 (the number of the secondary calibration spectra, "n") is predetermined. In other embodiments, the size of the secondary calibration matrix may be continuously updated or limited based upon certain variables such as elapsed time of measurement, orthogonality of the secondary calibration matrix to the principal calibration matrix, and the magnitude of the residual spectrum.

The residual magnitude threshold value used in the comparison step "exceed threshold?" 618 may be determined by experimentation, taking into account factors including the inherent random spectral noise, the number of spectral averaging which affects spectral noise, and the required stability of the measurement.

Figure 7:
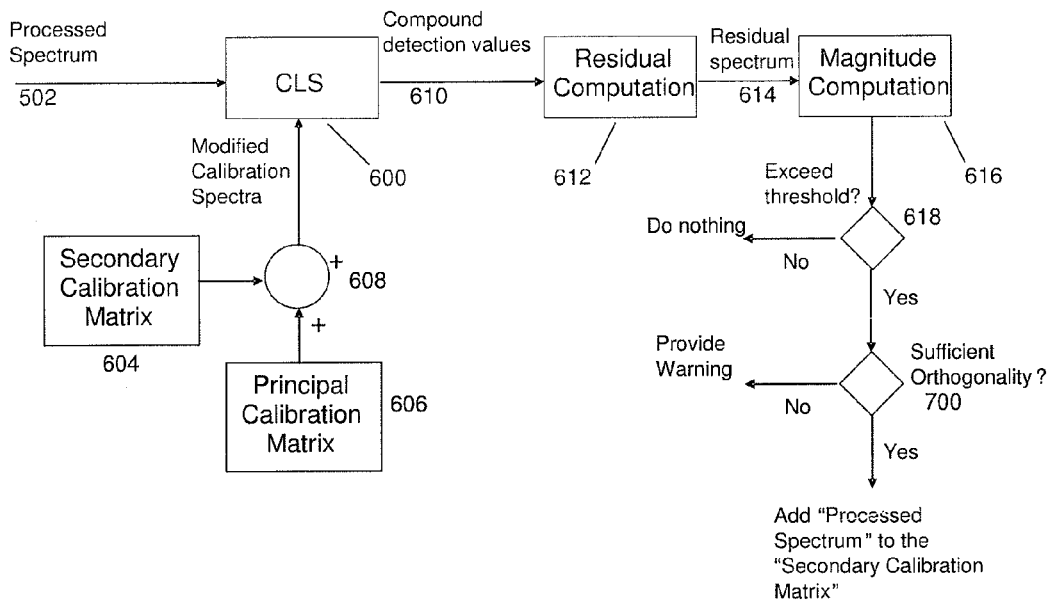
FIG. 7 is a flow chart for a spectral processing method using an adaptive algorithm according to an illustrative embodiment of the present invention.

FIG. 7 shows another embodiment of the adaptive algorithm, in which another condition, "sufficient orthogonality" 700 is added before a measured spectrum is added to the calibration matrix. In this embodiment, the measured spectrum is tested whether it is sufficiently orthogonal to each of the principal calibration spectrum. The test involves computing the inner dot product of the normalized vectors, s. k, where s is the normalized measured spectrum (not shown) and k is one of the normalized principal calibration spectra 606. The result would be between zero (completely orthogonal) and one (completely parallel). This test is important to ensure no spectrum that is considerably parallel to any of the spectra of the target compounds is entered into the calibration matrix. If that happens, the measurement results of the target compounds would be erroneous. An orthogonality test threshold value should be chosen to minimize this risk. In the present embodiment, that threshold value is chosen to be 0.05.

When the orthogonality criterion is not met, the processor 124 may be configured to produce a signal ("Provide Warning" 700) that can be used to alert the user in various ways, including flashing an LED, generating sounds, displaying messages, etc. The warning signal(s) tells the user that there are one or more interference compounds that have spectral features similar to one of the target compounds. The algorithm can also be designed such that the warning signal provide specific messages as to which target compound the interference compound is conflicting with.

Figure 8:
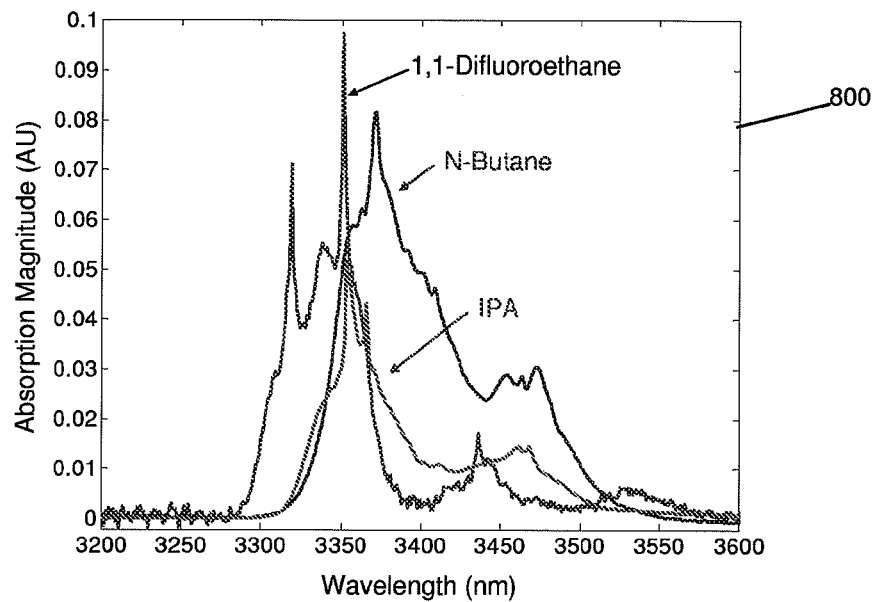
FIG. 8 is an illustration of spectral data from an experiment using a spectroscopic method according to an illustrative embodiment of the present invention.

The usefulness of the approach is demonstrated in the following experiment. A test unit was set up to monitor N-Butane gas as the target compound, one of the common hydrocarbons of interest in safety monitoring application. Isopropanol vapor (IPA) and 1,1-Difluoroethane gas were used as the interferents, both of which are commonly used cleaning compounds. Note that 1,1-Difluoroethane (R-152a) is commonly used as the main or sole ingredient of "dust-off" electronic cleaning products. The high-resolution absorption spectra (1 cm$^{-1}$ resolution) of the compounds between 3200 nm and 3600 nm are shown in FIG. 8. As seen, the spectra 800 are greatly overlapping. If a traditional chemometric method, such as the classical least-squares or principal component analysis technique is to be used, the spectra of both interferents must be entered into the calibration matrix. Otherwise, greatly erroneous readings would be produced. With an adaptive algorithm, on the other hand, the calibration matrix needs to contain only one spectrum, which is the spectrum of the target gas, N-Butane.

Figure 9:
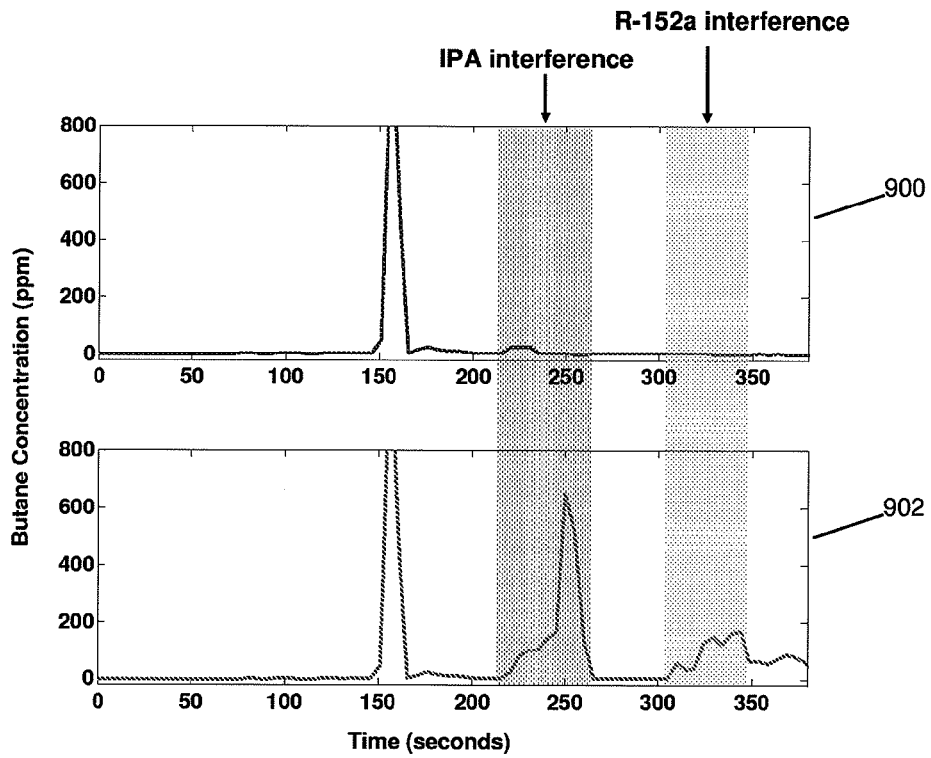
FIG. 9 is an illustration of spectral data from an experiment using a spectroscopic method according to an illustrative embodiment of the present invention.

1,1-Difluoroethane, one of the test interference gases was sampled by releasing it from "dust-off" product near in the inlet of the sampling port. Similarly, IPA vapor was sampled by opening a bottle of rubbing alcohol liquid near the sampling inlet. FIG. 9 demonstrates the ability of the system to compensate for the interfering compounds, IPA vapor and 1,1,-Difluoroethane gas. The top graph 900 shows butane concentration readings using an adaptive algorithm. The maximum butane concentration error was less than 25 ppm, which also quickly disappeared (within two measurement cycles). This happened when a large amount of IPA vapor was introduced. Note again that the spectrum of IPA vapor was not included in the calibration matrix. Without the adaptive algorithm, the maximum butane concentration error would have been more than 600 ppm due to the same interference release, as can be seen on the lower graph 902. Similarly, the interference compensation technique worked well for the R-152 interference, in which the system exhibited negligible error.

Wavelength Lock

Figure 10:
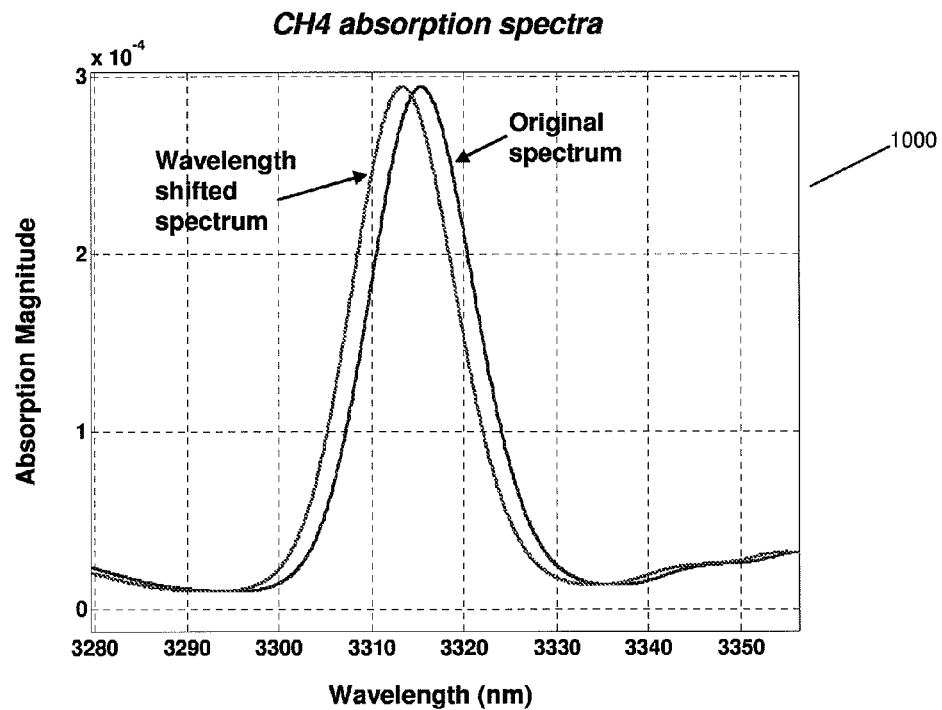
FIG. 10 is an illustration of wavelength scale error caused by wavelength shift.

Another source of measurement instability is wavelength scale variations due to optical alignment changes, inherent temperature dependence of the optical interference filter 3 and/or temperature dependence of the compound's spectral features themselves. Interference optical filters will shift to longer wavelength with increasing temperature and shorter wavelength with decreasing temperature. The shift is on the order of 0.01-0.2 nm/deg. Celsius. For example, a 10 deg. Celsius shift of temperature could amount to 2 nm of wavelength scale variation, which would degrade measurement stability. FIG. 10 illustrates a wavelength scale error causing an apparent shift in the absorption spectrum of the sample, potentially causing a significant measurement error using traditional least-squares, chemometrics approach.

Figure 11:
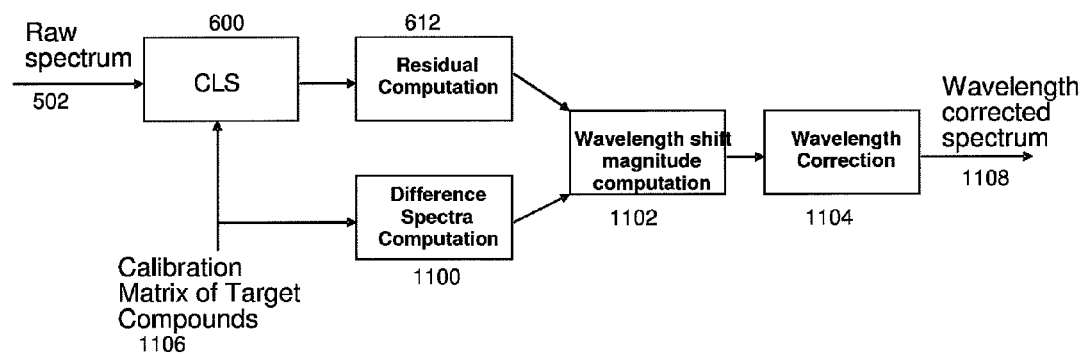
FIG. 11 is a block diagram of a method for correcting for wavelength scale error according to an illustrative embodiment of the present invention.

A "wavelength lock" algorithm is used to compensate for the wavelength error by wavelength shifting the measurement spectrum prior to the least squares prediction. A block diagram depicted in FIG. 11 shows the flow chart of the methodology. The raw spectrum 502, presumed to contain wavelength error, is modeled using a classical least squares algorithm (CLS) 600 (explained below) or other similar approach to obtain the spectrum residual, i.e. the "left-over" part of the spectrum that is not fitted by the model. CLS regression involves the following computation:

$$c = sK^T(KK^T)^{-1}$$

where c is a vector containing the concentration value(s), s is the sample spectrum, and K is the calibration matrix 1106 containing pre-determined basis spectra. The residual spectrum, r, is obtained by performing the following computation:

$$r = s - c^T K^T$$

Figure 12:
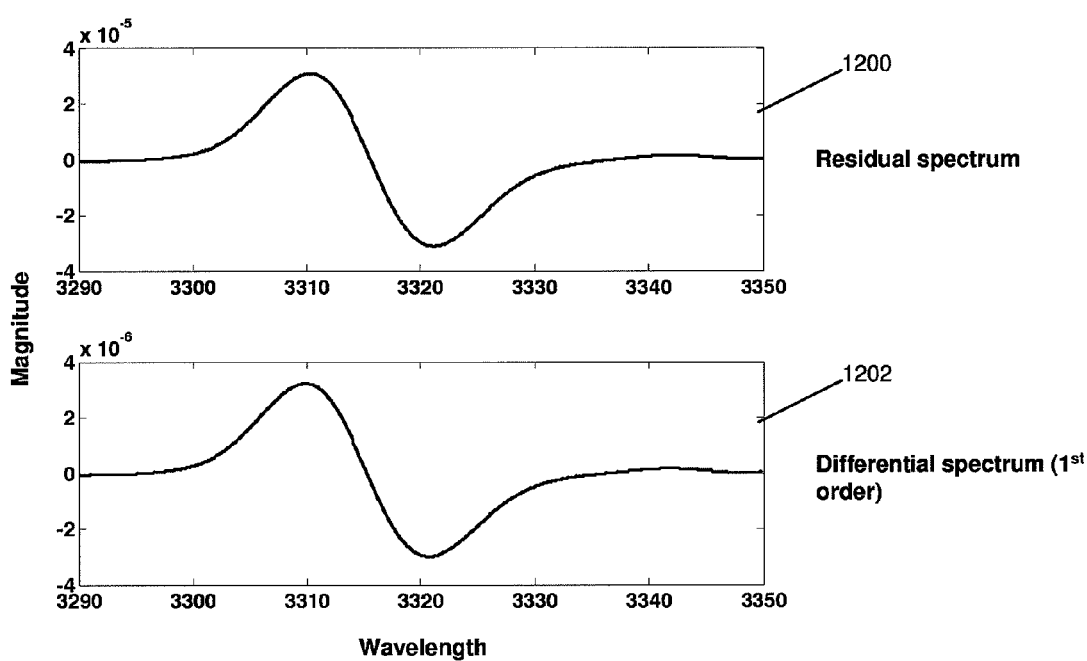
FIG. 12 is an illustration of residual spectrum due to wavelength error mismatch and a first order difference spectrum.

The presence of wavelength shift causes a classical least-squares regression (CLS) residual spectrum 612 to have similar feature characteristics with a first order difference spectrum 1100. To illustrate by means of an example, consider the $CH_4$ spectra shown in FIG. 10. Using the original spectrum as the calibration spectrum (as the K matrix) and the wavelength shifted spectrum as the sample spectrum, s, the resulting residual spectrum, r, is computed and shown in the top figure 1200 of FIG. 12. The first order difference spectrum of the original spectrum, on the other hand, is shown in the bottom figure 1202 of FIG. 12. As seen, the residual spectrum and the first order difference spectrum exhibit great similarities, as expected. In addition, the magnitude of the residual spectrum, computed in the step Wavelength shift magnitude computation 1102 is proportional to the magnitude of the wavelength shift error. These features are used to correct the wavelength shift error as a step Wavelength correction 1104 to obtain a wavelength corrected spectrum 1108. This wavelength error correction algorithm may be applied continuously at a predetermined interval, as rapid as once every scan.

Other methods may be used to correct the wavelength shift error. One method includes monitoring the location of the peak of the spectrum. For example, the spectral peak at ~3315 nm in FIG. 10 is monitored to indicate the presence of wavelength shift. Such a method provides lower sensitivity to wavelength shift. In addition, the presence of other spectral features or peaks (such as those due to background or interfering compounds) may obscure the result.

Multi-Region, Cross-Analysis Regression

Figure 13:
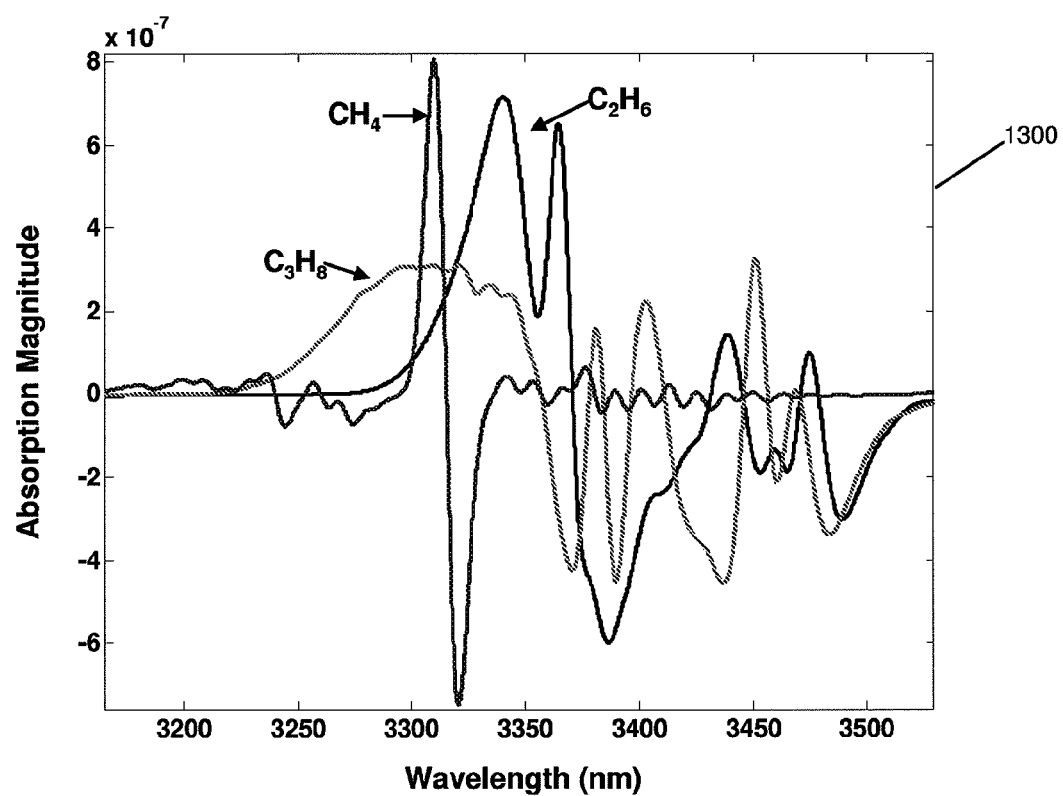
FIG. 13 is an illustration of first order absorption spectra of various compounds in a mid-IR region.
Figure 14:
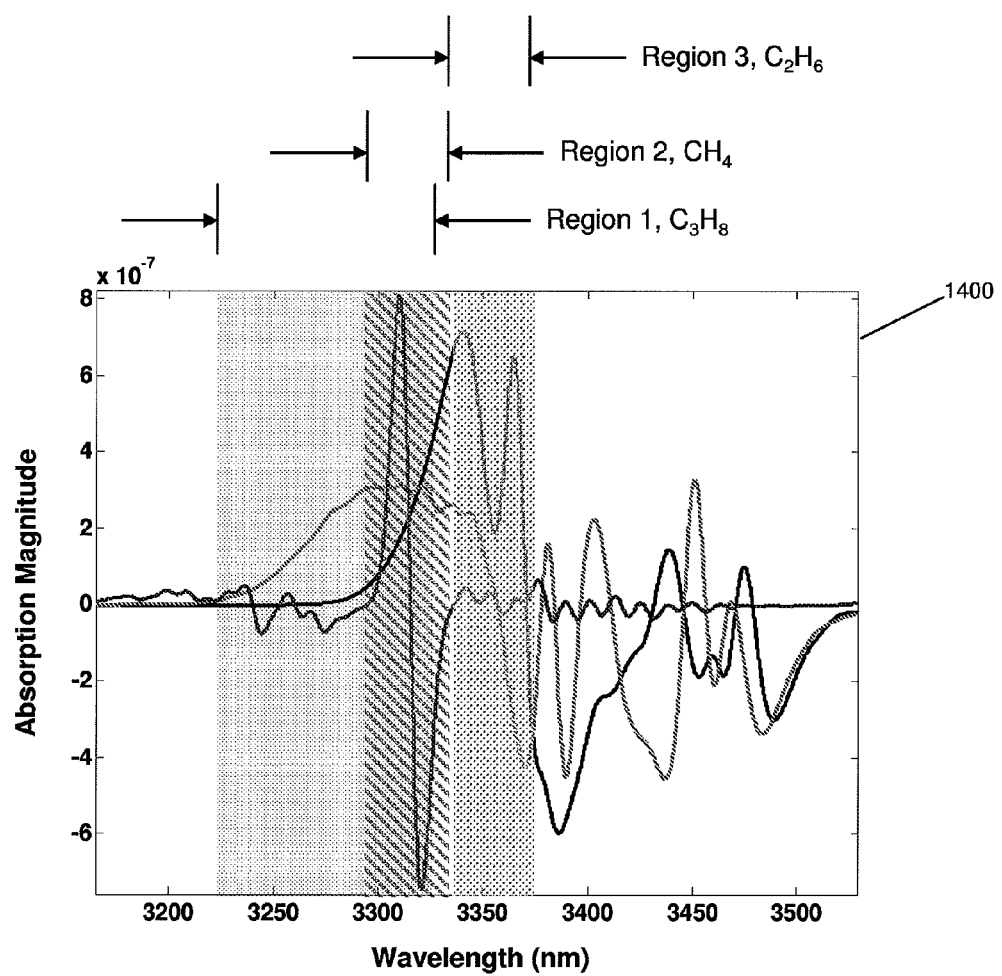
FIG. 14 is an illustration of multi-region, cross-analysis band selection.

To further enhance measurement sensitivity and selectivity, and to minimize the effects of spectral non-linearities, a multi-band, cross-analysis, least-squares regression is used. The least-squares regression approach uses a single analysis band or region to measure the target compound(s), i.e. using a single calibration matrix, K, over a certain wavelength region. On the other hand, the multi-band, cross-band regression method uses multiple K calibration matrices for a single or multiple target compounds. To illustrate by means of an example, we consider an application where the spectroscopic device is used to measure the concentrations of methane ($CH_4$), ethane ($C_2H_6$) and propane ($C_3H_8$) vapors in a certain process stream or in the ambient air. FIG. 13 shows the first order absorption spectra of the vapors in the relevant mid-infrared region. The traditional approach uses a single region covering the whole relevant wavelength region, for example, between 3200 and 3500 nm to perform the analysis using a certain chemometrics algorithm such as CLS, PLS or PCA. One embodiment makes use of multiple regions to perform the analysis, building multiple calibration matrices and using them simultaneously to perform the compound concentrations computation. FIG. 14 shows possible separate band regions, regions 1, 2 and 3 for the analysis, each containing a calibration matrix "tuned" for the analysis of one target compounds.

Figure 15:
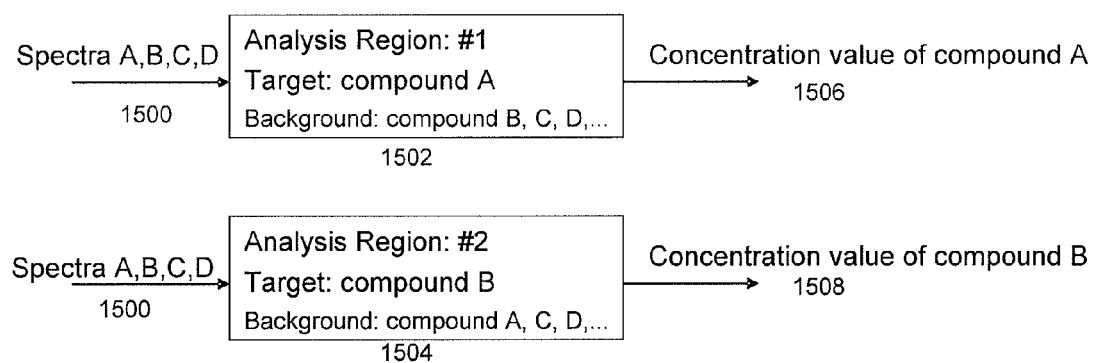
FIG. 15 is a block diagram of a method for multi-region, cross-analysis band selection according to an illustrative embodiment of the present invention.

Furthermore, each calibration matrix (at each region) includes the models for some of all of the other compounds present in the sample, to account for their interferences. Following the previous example, the calibration matrix for $C_3H_8$ (using region 1) would contain the models to account for the spectral features of $CH_4$ and $C_2H_6$ located within region 1 to minimize the interference or cross-sensitivity effects. FIG. 15 illustrates the general approach. For example, analysis of region 1, 1502, corresponding to target compound A and intereferents B, C, and D 1500, can yield concentration values of compound A, 1506. Similarly, analysis of region 2, 1504, yields concentration value of compound B, 1508.

Figure 16:
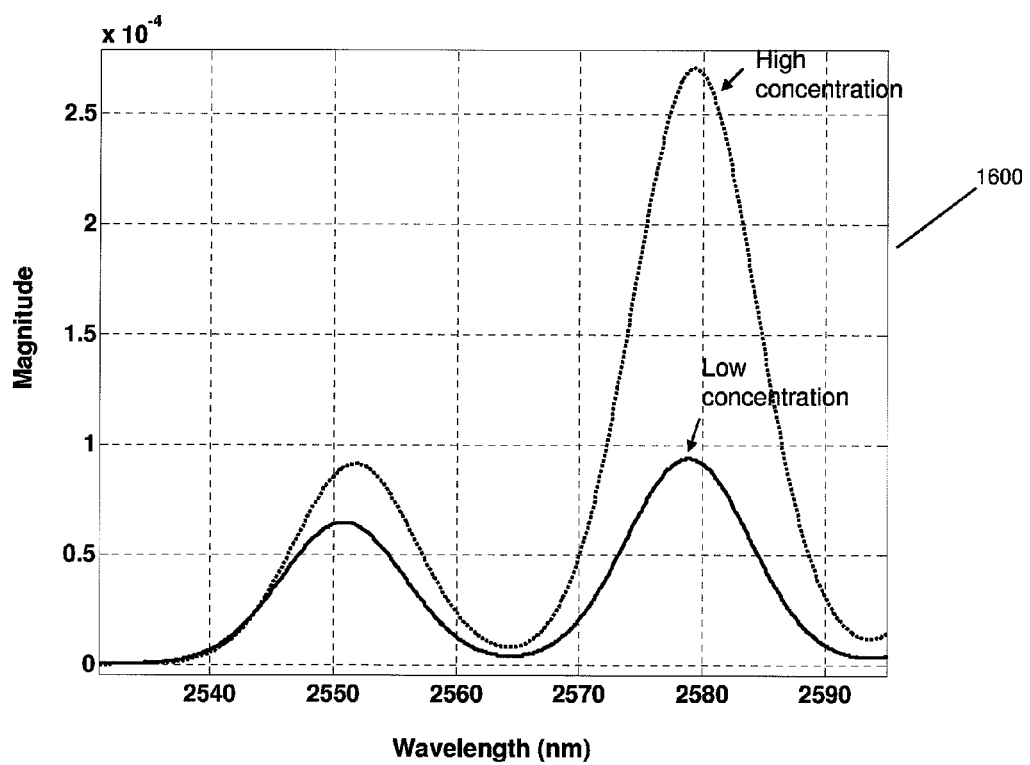
FIG. 16 is an illustration of potential non-linear spectral error caused by wavelength-dependent spectral magnitude variations.
Figure 17:
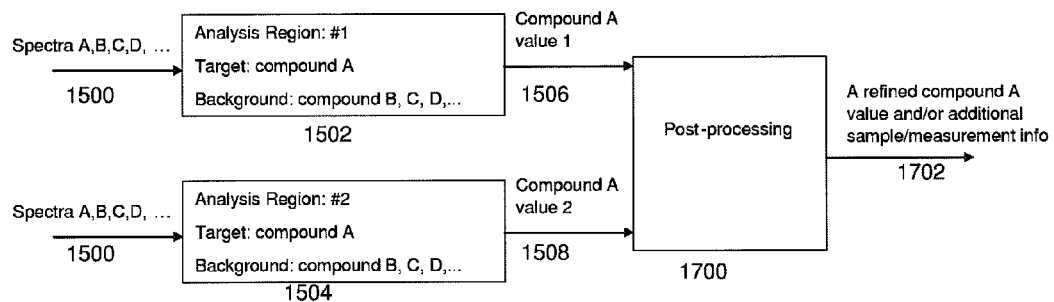
FIG. 17 is a block diagram of a method of multi-region, cross analysis regression according to an illustrative embodiment of the present invention.

Furthermore, more than one analysis region may be used to compute the value of a single compound, resulting in more than one computed concentration or density values. These computed values may later be post-processed to produce a single value or other information. Such a method is particularly advantageous in a highly complex sample mixtures, high-concentration samples or highly scattering samples, where non-linear behaviors are present. To illustrate the method by means of example, consider an absorption spectrum shown in FIG. 16, in particular, notice how an increase in concentration or density value affect the magnitude of the absorption spectrum. Instead of uniform or constant magnitude amplification across the wavelengths, the amplification itself is wavelength dependent. As such, a single-region analysis using a linear least-squares regression will result in a large residual error and will not provide an accurate concentration or density computation. The multi-region, cross-analysis regression method solves the problem by breaking the wavelength region into smaller pieces, each producing a computed concentration or density value. The concentration or density values are then post-processed 1700 to produce a single concentration or density value and/or other pertinent information related to the state of the sample or measurement 1702. The general approach is illustrated in FIG. 17.

Single-Beam Based Correction

A potential source of spectral baseline instability is instrumental variations, such as light source degradation and power variations, optics transmission degradation due to dust and particulates, alignment changes, etc. The spectral characteristics of most if not all of the instrumental variations can be modeled from the spectral characteristics of the single beam spectrum itself. The single-beam spectrum refers to the transmission spectrum of an EM radiation source and the optical system without the presence of a sample. The predicted spectral features of these potential variations (the instrument-correction spectra) are derived from the single-beam spectrum and entered into the calibration matrix. The instrument-correction spectra may be in the form of the pure single-beam spectrum, the derivative(s) of the single-beam spectrum and/or other derivations of the single-beam spectrum.

Background Calibration Method

Certain embodiments of the invention include development of a calibration matrix, in particular, a "background" calibration set, $S_{background}$, i.e. a set containing the spectra of all of the interfering background samples except for the target compound, separately from the target compound's calibration set, $S_{target}$. Two separate calibration sets are produced, one that of the background, and one that of the target compound.

The background calibration set is developed by intentionally varying the concentration or density levels of the background interfering compounds. The background calibration set may also include the spectral variations model due to instrumental changes such as light source intensity changes. Similarly, these instrumental variations shall be simulated intentionally to build a calibration set that completely and accurately models all of the potential variations. Care should be taken to ensure that the samples used to develop the background calibration set do not include any detectable level of the target compounds. A background calibration matrix is then developed by reducing the spectral variations in the background calibration set into a smaller orthogonal set of variations using PCA (principal component analysis), PLS (partial least squares) or other similar methods. In using PLS, the dependent variables input would be a vector of zeroes, due to zero values of the target compound in all of the samples.

Independently, the calibration set of the target compound is developed by varying its levels of concentration or density within the relevant range. Care should be taken so as not to introduce any impurities that might have interference effects to the recorded spectra. For example, in the case of infrared gas absorption measurement, nitrogen or helium may be used as the balance gas in the calibration set development as neither exhibit any infrared absorption signals.

The background and target compound calibration sets are then combined to produce the calibration matrix. To illustrate by means of example, suppose 100 spectra are obtained for the background set and 10 spectra are obtained for the target compound set. The complete calibration set will contain 110 spectra upon which the calibration matrix is developed.

If there is more than one target compound, the previous steps are repeated for each additional target compound. Interference between the target compounds shall be taken into account by including the spectra of any other target compounds as part of the background calibration set of the subject target compound.

Light Source Power Modulation

Figure 18:
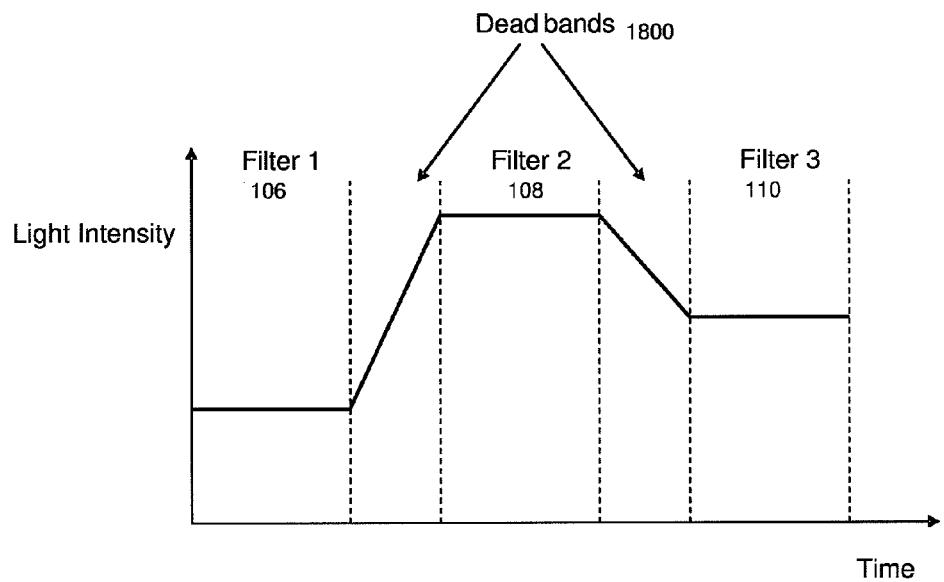
FIG. 18 is an illustration of programmatically varying light source intensity with dead band regions.

To further optimize the system components' dynamic range and/or to provide better detections of compounds having weak signals without increasing the overall power requirement, the EM radiation source(s) 100 may be varied in its intensity by varying the source voltage or current programmatically, so as to provide higher or lower intensity depending on the spectral range that is being analyzed at each particular instant. FIG. 18 shows an example of an EM radiation intensity variation profile. In this example, the EM radiation source intensity is programmed such that each filter analysis region uses a constant source intensity. In another embodiment, the light source intensity may be varied within each or any of the filter analysis regions. As the filter assembly 104 rotates, the path of the beam of EM radiation will become incident on both active and inactive portions of each filter. As the beam is incident on an inactive portion, a dead band 1800 is produced. In an embodiment, the EM radiation source 100 is modulated in such a way so that the power is zero or close to zero in the dead bands 1800, to minimize the average power dissipation.

Figure 19:
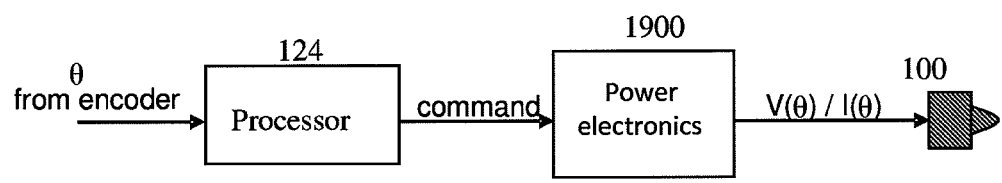
FIG. 19 is a block diagram for a method of modulating the intensity of an electromagnetic radiation source according to an illustrative embodiment of the present invention.

In certain embodiments, the modulation command is originated in the processor 124, which uses the angular position of the filter assembly 104 from the encoder electronics 206 to determine the level of source intensity to output. The output (generally in the form of a voltage) of the processor 124 enters the EM radiation source power electronics, which is configured to vary the voltage (in the case of voltage mode EM radiation source) or current (in the case of current mode EM radiation source), and thus varying the resulting intensity of the EM radiation source 100. The processor contains an algorithm which is used to compute the command signal based on the angular position info from the encoder 208. A block diagram illustrating the method is shown in FIG. 19. In another embodiment, the EM radiation source intensity is switched between various predetermined levels such as low, med and high, using trigger based switch electronics, rather than a processor.

One possible limitation to this EM radiation modulation method is the bandwidth of the EM radiation source(s). Traditional black body sources such as those using tungsten or kanthal filaments have low bandwidths, and thus have generally been used for steady state application. However, some of today's black body sources are designed with filament designs that are capable of bandwidths up to 50 Hz or more. LED (Light Emitting Diode) and SLED (Super Luminescence Diode) light sources are capable of higher modulation bandwidths.

Figure 20:
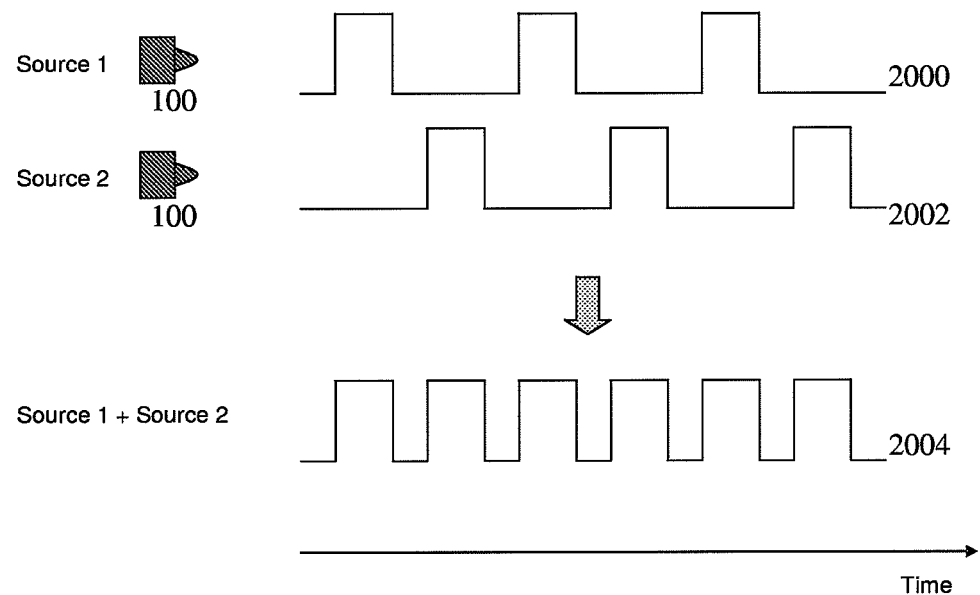
FIG. 20 is an illustration of synchronizing two EM radiation sources to obtain higher modulation bandwidth, according to an illustrative embodiment of the present invention.

In the case of black body sources, the bandwidth capability can be increased by employing more than one source, synchronized to provide a series of modulations or pulses at a higher frequency or duty cycle than obtainable with one source. FIG. 20 illustrates an implementation of this concept where two EM radiation sources 100 are used synchronically to double the pulse frequency from what is obtainable by a single source. In one embodiment, the beams from the EM radiation sources 100 are combined through collecting and collimating optical elements and directed into the rotating filter assembly 104. In another embodiment, the filaments are packaged in a single collecting optics unit, such as a TO-8 package, with or without an integrated collimating optics.

Multiple Light Sources and/or Detectors Covering Multiple Wavelength Region

More than one EM radiation source 104 and/or EM radiation detector 116 may be used to increase the spectral coverage of the system. Some applications require analysis in multiple wavelength regions that are not effectively covered by a single EM radiation source and detector. In continuous emission monitoring application, for example, the system needs to monitor CO, $CO_2$ and NOx in streams containing high level of moisture. While CO and $CO_2$ are best analyzed in the mid-infrared region, NOx is best analyzed in the UV region due to its large interference with water vapor spectrum. There is no single EM radiation source or detector that can effectively cover the UV and IR regions simultaneously. A wavelength selective device of this invention may be combined with multiple EM radiation sources and detectors, providing a novel integrated system. Another example requiring multiple source arrangement is one where the EM radiation sources are LED or SLED types where each only covers a certain narrow band region. In such a case, multiple sources may used with a single detector element.

Figure 21:
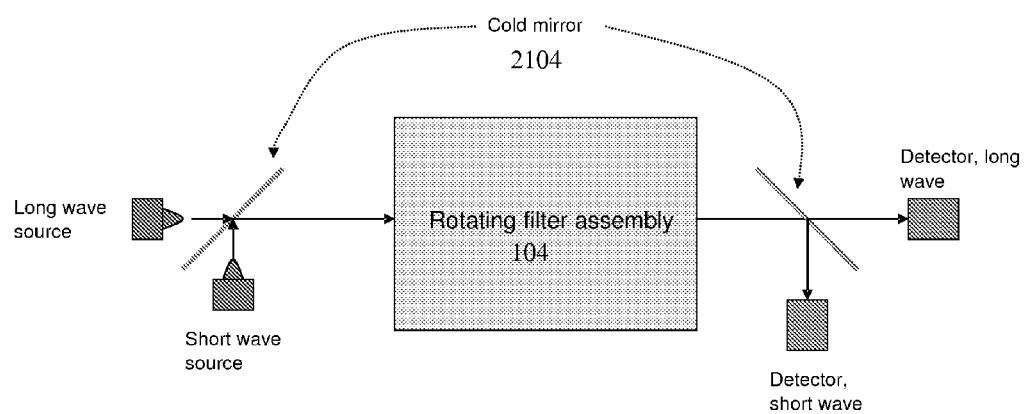
FIG. 21 is an illustration of the use of two EM radiation sources and two detectors for multi-wavelength region analysis, according to an illustrative embodiment of the present invention.

In one embodiment, the EM radiation beams from the sources 100 are combined using cold/hot mirrors 2104 with a long/short wavelength pass filter or beamsplitter on the source and detector side. The concept is illustrated in FIG. 21. Multiple of these "beam combiner/splitter" elements may be used for more than two sources and/or two detectors. In another embodiment, the EM radiation sources 100 are packaged as an integrated element, producing a single EM radiation beam output.

Stacked Filter Assemblies

Figure 25:
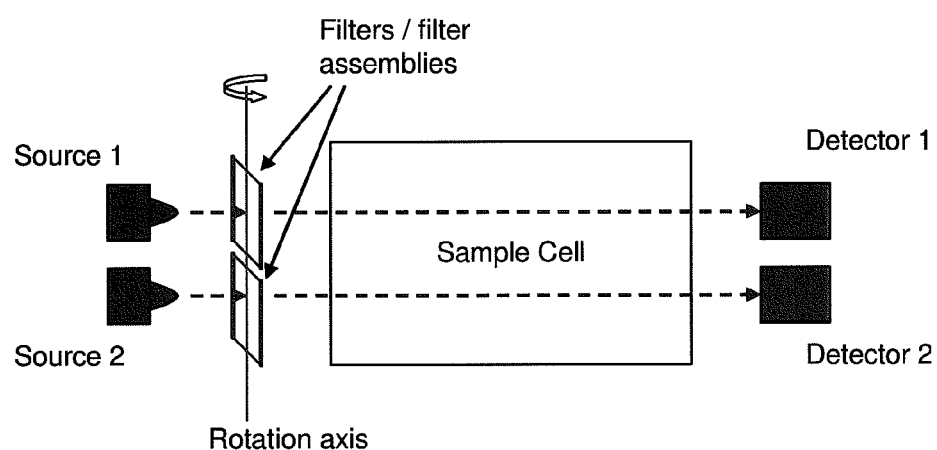
FIG. 25 is an illustration of a configuration employing stacked filter assemblies, according to an illustrative embodiment of the present invention.

Another configuration or feature of the rotating filter spectroscopic system is that of stacked filters or filter assemblies, where the two or more filters or filter assemblies are stacked along the rotation axis. FIG. 25 illustrates the concept of the mechanical layout. One or more sources and detector may be used. When one source or detector is used, the beam may be split or combined using beam-splitters, beam-combiners, cold filters, hot filters and other equivalent functioning optics. The purpose of the stacked filters or filter assemblies may include: (i) increasing the number of wavelength bands that can be covered with a single motor assembly and/or (ii) covering multiple wavelength bands that need to use two different sources and/or detectors such as the UV and the IR region using a single motor assembly.

Differential Measurement of Process or Reaction Monitoring

Figure 22:
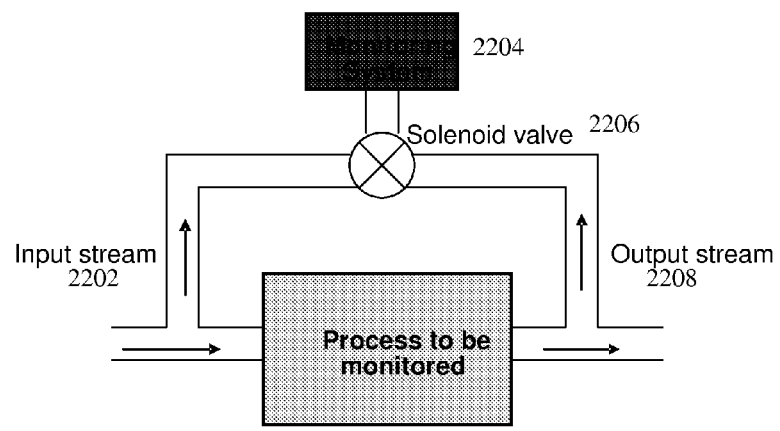
FIG. 22 is a process flow diagram for a spectroscopic method using sequential, differential measurement according to an illustrative embodiment of the present invention.

A differential measurement method may be used for monitoring certain processes such as filtration, purification, chemical and biological reaction where comparison is made between the input and the output streams. The concept is illustrated in FIG. 22. The process input and output streams can be selected and sampled sequentially at predetermined intervals using a solenoid valve 2206, as depicted in FIG. 22. A monitoring system 2204 is used to obtain spectrum from samples taken from the input and output streams. A spectrum obtained from one of the streams (input stream 2202 or output stream 2208) is stored as the "zero" or baseline spectrum. The spectrum obtained from the other stream is then referenced to the zero spectrum. In an absorption spectroscopy measurement, the absorption spectrum $A(\lambda)$ is obtained by applying the following mathematical function:

$$A(\lambda) = \log_{10}\{T_{input}(\lambda)/T_{output}(\lambda)\}$$

where $T_{input}$ and $T_{output}$ are the spectra of the input stream and the output stream respectively, and they may be interchanged in the above equation. The above method reduces or even eliminates potential drift or measurement instabilities due to instrumental and/or environmental changes. Furthermore, the method would reduce the effects of background interferences.

Figure 28:
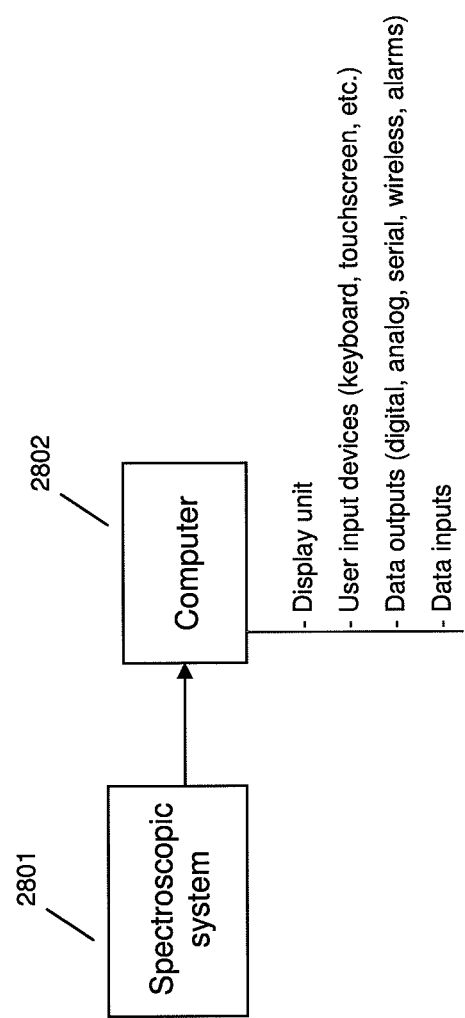
FIG. 28 is a block diagram illustrating the spectroscopic system in communication with a computer and its elements, according to an illustrative embodiment of the present invention.

As illustrated in FIG. 28, the spectroscopic system 2801 may include a computer or may otherwise share input and output with a computer 2802 (e.g., a computer internal or external to the spectroscopic system), the computer including software for digitizing, receiving, storing, and or processing data corresponding to the detected electromagnetic radiation and/or signals created by such detected electromagnetic radiation. The computer may also include a keyboard or other portal for user input, and a screen for display of data to the user. The computer may include software for process control, data acquisition, data processing, and/or output representation. The spectroscopic system may include a wireless system for acquisition of data and/or system control. For example, the wireless system may allow wireless data transfer from and/or to a computer, allowing wireless input and/or output (and/or system control) by/to a user via a user interface connected to the computer, such as a keyboard and/or display screen.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims. The relevant teachings of all the references, patents and patent applications cited herein are incorporated herein by reference in their entirety.

What is claimed is:

1. A spectroscopic system for detecting electromagnetic radiation that has passed through or is reflected from a sample, the system comprising:
   an electromagnetic radiation source;
   a rotatable filter assembly configured to filter a beam of electromagnetic radiation produced by the electromagnetic radiation source;
   a position detector configured to detect a position of the rotatable filter assembly; and
   an electromagnetic radiation detector configured to detect electromagnetic radiation that has passed through or is reflected from a sample, wherein the rotatable filter assembly is configured to rotate about an axis non-perpendicular to a path of the beam of electromagnetic radiation, where an angle between the axis of rotation of the rotatable filter assembly and the path of the beam of electromagnetic radiation is in a range from 60 degrees to 89.99 degrees.

2. The spectroscopic system of claim 1, comprising a plurality of electromagnetic radiation sources.

3. The spectroscopic system of claim 2, comprising a plurality of electromagnetic radiation detectors.

4. The spectroscopic system of claim 1, wherein the rotatable filter assembly comprises at least one filter having a surface parallel to the axis of rotation of the rotatable filter assembly.

5. The spectroscopic system of claim 1, wherein the angle between the axis of rotation and the path of the beam of electromagnetic radiation is from 60 degrees to 85 degrees.

6. The spectroscopic system of claim 1, wherein the rotatable filter assembly comprises a plurality of filters.

7. The spectroscopic system of claim 1, comprising a controller configured to adjust a rotational velocity of the rotatable filter assembly.

8. The spectroscopic system of claim 1, wherein the rotatable filter assembly comprises stacked filters, with two or more stacks along the axis of rotation.

9. The spectroscopic system of claim 1, comprising one or more additional filter assemblies and one or more additional motors coupled to the one or more additional filter assemblies.

10. The spectroscopic system of claim 1, wherein the position detector comprises an encoder configured to produce at least a first signal comprising a series of digital pulses at a first frequency, each digital pulse corresponding to an angular position of the rotatable filter assembly.

11. The spectroscopic system of claim 10, wherein the first frequency is a clock frequency.

12. The spectroscopic system of claim 10, wherein the encoder is configured to produce a second signal, and wherein the spectroscopic system comprises an encoder signal processing module configured to combine the first and second signals into a third signal.

13. The spectroscopic system of claim 12, wherein the third signal comprises a series of digital pulses having at least double the first frequency.

14. The spectroscopic system of claim 10, wherein the encoder comprises an edge detector configured to detect an edge of each of at least two signals produced by the encoder and to thereby produce a signal comprising a series of digital pulses having at least quadruple the first frequency.

15. The spectroscopic system of claim 10, wherein the encoder is rigidly attached to the rotatable filter assembly.

16. The spectroscopic system of claim 10, wherein the encoder is configured to produce significantly more digital pulses per rotation of the rotatable filter assembly than are necessary to accurately produce an analog signal from the electromagnetic detection detector, wherein the encoder is configured to digitize the analog signal with at least 1000 pulses per rotation of the rotatable filter assembly.

17. The spectroscopic system of claim 1, comprising a variable gain amplifier configured to convert a light signal from the electromagnetic radiation detector into an electrical signal, wherein the variable gain amplifier is in communication with the position detector and is configured to automatically adjust a gain profile of a signal received from the electromagnetic radiation detector based on a detected angular position of the rotatable filter assembly.

18. The spectroscopic system of claim 1, comprising a variable gain amplifier configured to convert a light signal from the electromagnetic radiation detector into an electrical signal wherein the amplifier is configured to automatically adjust a gain profile of a signal received from the electromagnetic radiation detector based on a magnitude of the signal.

19. The spectroscopic system of claim 1, comprising a processor configured to apply a convolution function to a spectral signal from the electromagnetic radiation detector, thereby enhancing wavelength stability and/or repeatability, and/or thereby improving signal-to-noise ratio.

20. The spectroscopic system of claim 1, wherein a processor is configured to apply a baseline correction algorithm to a spectral signal from the electromagnetic radiation detector, thereby enhancing long-term measurement stability.

21. The spectroscopic system of claim 1, comprising a plurality of electromagnetic radiation sources, thereby enabling detection of electromagnetic radiation over a broader spectrum and/or over multiple spectra.

22. The spectroscopic system of claim 21, wherein the plurality of electromagnetic radiation sources comprise a UV radiation source and an IR radiation source.

23. The spectroscopic system of claim 1, comprising:
a motor coupled to the rotatable filter assembly.

24. The spectroscopic system of claim 1, wherein the beam of electromagnetic radiation is a collimated beam, and wherein the rotatable filter assembly is configured to rotate about an axis non-perpendicular to the path of the collimated beam of electromagnetic radiation.

25. A spectroscopic method for detecting electromagnetic radiation that has passed through or is reflected from a sample, the method comprising:
filtering a beam of electromagnetic radiation produced by an electromagnetic radiation source with a rotatable filter assembly;
detecting an angular position of the rotatable filter assembly with a position detector having at least one component rigidly coupled to the rotatable filter assembly;
intercepting the beam of electromagnetic radiation with a sample;
detecting the beam of electromagnetic radiation with an electromagnetic radiation detector; and
processing a spectral data signal from the electromagnetic radiation detector to produce chemical information about the sample,
wherein the rotatable filter assembly is configured to rotate about an axis non-perpendicular to a path of the beam of electromagnetic radiation, where an angle between the axis of rotation of the rotatable filter assembly and the path of the beam of electromagnetic radiation is in a range from 60 degrees to 89.99 degrees.

26. The spectroscopic method of claim 25, wherein the rotatable filter assembly comprises a narrow-band interference filter.

27. The spectroscopic method of claim 25, wherein the rotatable filter assembly comprises at least three filters.

28. The spectroscopic method of claim 25, wherein the beam of electromagnetic radiation is a collimated beam, and wherein the rotatable filter assembly is configured to rotate about an axis non-perpendicular to a path of the collimated beam of electromagnetic radiation.

* * * * *